US012697205B2

(12) United States Patent
Naftali et al.

(10) Patent No.: US 12,697,205 B2
(45) Date of Patent: Aug. 4, 2026

(54) INTRAOCULAR LENS FIXATION DEVICE

(71) Applicant: RAMBAM MEDTECH LTD., Haifa (IL)

(72) Inventors: Modi Naftali, D.N. Gilboa (IL); Yinon Shapira, Ramat Gan (IL)

(73) Assignee: RAMBAM MEDTECH LTD., Haifa (IL)

( * ) Notice: Subject to any disclaimer, the term of this patent is extended or adjusted under 35 U.S.C. 154(b) by 629 days.

(21) Appl. No.: 18/031,783

(22) PCT Filed: Oct. 7, 2021

(86) PCT No.: PCT/IL2021/051201
§ 371 (c)(1),
(2) Date: Apr. 13, 2023

(87) PCT Pub. No.: WO2022/079710
PCT Pub. Date: Apr. 21, 2022

(65) Prior Publication Data
US 2023/0380959 A1      Nov. 30, 2023

Related U.S. Application Data

(60) Provisional application No. 63/091,374, filed on Oct. 14, 2020.

(51) Int. Cl.
*A61F 2/16*       (2006.01)
*A61F 2/14*       (2006.01)

(52) U.S. Cl.
CPC ................ *A61F 2/16* (2013.01); *A61F 2/148* (2013.01); *A61F 2002/1681* (2013.01); *A61F 2210/0014* (2013.01); *A61F 2220/0008* (2013.01)

(58) Field of Classification Search
CPC .... A61F 2/148; A61F 2/16; A61F 2002/1681; A61F 2210/0014; A61F 2220/0008; A61F 2220/0016; A61F 9/007
See application file for complete search history.

(56) References Cited

U.S. PATENT DOCUMENTS 3,996,626 A      12/1976   Richards et al.
4,124,905 A  *   11/1978   Clark ........................ A61F 2/16
                                                 623/6.38
(Continued)

FOREIGN PATENT DOCUMENTS

CN       204147166 U     2/2015
WO       2004/082488 A1   9/2004
(Continued)

OTHER PUBLICATIONS

An International Search Report and a Written Opinion both dated Dec. 7, 2021, which issued during the prosecution of Applicant's PCT/IL2021/051201.
Little, B. C., et al. "Trans-scleral fixation of dislocated posterior chamber intraocular lenses using a 9/0 microsurgical polypropylene snare." Eye 7.6 (1993): 740-743.
(Continued)

*Primary Examiner* — Mohamed G Gabr
(74) *Attorney, Agent, or Firm* — Sughrue Mion, PLLC

(57)          ABSTRACT

An ocular clip implant (22) used for securing an intraocular lens (IOL) (62) in an eye of a patient is provided which includes an IOL-engaging portion (26) disposed at a first end of the ocular clip implant (22). The IOL-engaging portion (26) is configured to grasp a portion of the IOL (62). An ocular-wall-engaging portion (28) is integrated with and disposed at a second end of the ocular clip implant (22). The ocular-wall-engaging portion (28) includes an anchor (29) transitionable from a first, straightened configuration to a second, non-straightened configuration to anchor the ocular clip implant (22) to a wall of the eye in order to secure the IOL (62) to the eye. Other embodiments are also described.

15 Claims, 16 Drawing Sheets

(56) References Cited

U.S. PATENT DOCUMENTS

| | | | |
|---|---|---|---|
| 4,214,585 A * | 7/1980 | Bailey, Jr. | A61F 2/1608 |
| | | | 623/4.1 |
| 8,419,790 B1 | 4/2013 | Sabti | |
| 9,055,939 B2 | 6/2015 | Fujisaki et al. | |
| 9,277,994 B2 | 3/2016 | Miller et al. | |
| 2006/0135969 A1 | 6/2006 | Assia | |
| 2006/0259049 A1 | 11/2006 | Harada et al. | |
| 2008/0147083 A1 | 6/2008 | Vold et al. | |
| 2010/0057094 A1 | 3/2010 | Akahoshi | |
| 2013/0006271 A1 | 1/2013 | Vold et al. | |
| 2016/0022488 A1 | 1/2016 | Dimmig et al. | |
| 2016/0183946 A1 | 6/2016 | Vold et al. | |
| 2019/0000609 A1 | 1/2019 | Hamill | |

FOREIGN PATENT DOCUMENTS

| | | | |
|---|---|---|---|
| WO | 2014/138615 A1 | 9/2014 | |
| WO | 2018/172897 A1 | 9/2018 | |

OTHER PUBLICATIONS

U.S. Appl. No. 63/091,374, filed Oct. 14, 2020.
Communication dated Jun. 17, 2024 issued by the European Patent Office in application No. 21879653.0.
Jeffrey L. Olson, MD, et al., "Intraocular lens fixation with a 30-gauge injectable shape-memory alloy clip in a porcine eye", Journal Cataract and Refractive Surgery, vol. 38, Jun. 2012, pp. 1105-1106.

* cited by examiner

INTRAOCULAR LENS FIXATION DEVICE

CROSS-REFERENCE TO RELATED APPLICATIONS

The present application is the U.S. national stage of International Application of PCT/IL2021/051201, filed Oct. 7, 2021, which claims priority from U.S. Provisional Patent Application 63/091,374 to Naftali et al., filed Oct. 14, 2020, entitled "Intraocular lens fixation device," and which is incorporated herein by reference.

FIELD OF THE INVENTION

The present application relates to a device and procedures performed on an eye of a patient. In particular, the present application relates to methods and devices for correcting dislocation/subluxation of an intraocular lens.

BACKGROUND

An intraocular lens (IOL) is an artificial lens implanted in the eye as part of a treatment for cataracts or myopia. These are implanted during cataract surgery, after the cloudy eye's natural lens has been removed. Some postoperative complications may arise, such as, the IOL can move and become displaced inside the eye postoperatively or be placed incorrectly by the operating surgeon. One such complication is post-surgical dislocation or subluxation of the lens in which the IOL becomes decentered away from the visual axis or into the posterior segment. Subluxated IOLs can produce such extreme decentration that the IOL optic covers only a small portion of the pupillary space. Luxation involves total dislocation of the IOL into the posterior segment.

US Patent Application Publication 2016/0022488 to Dimmig, et al., describes techniques and instrumentation for repositioning an intraocular lens (IOL) that becomes dislocated, such as following cataract surgery. In some methods, a trocar or sheath is placed through the eye wall near the ciliary body until a distal tip of the instrument is near the intraocular target to be moved. A clip or other engagement structure at the end of the instrument is manipulated to engage a portion of the IOL, such as a haptic, using various disclosed engagement mechanisms. The instrument is then manipulated to reposition the target to a desired position. In some cases, sutures are attached to the target or to the clip and then secured on the external surface of the eye to secure the target in the desired position.

SUMMARY OF THE APPLICATION

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

In some applications of the present invention, devices and methods are described herein for securing, and optionally repositioning an intraocular target, such as an intraocular lens (IOL), in the eye, using an ocular clip implant.

An introduction instrument is inserted through a wall of the eye into the eye in order to access the IOL. Typically, the introduction instrument is inserted directly into the eye and without the need for any trocars. The introduction instrument is then used to engage the IOL itself and reposition the IOL within the eye by moving the IOL using the introduction instrument. The introduction instrument is used to position an implant comprising an ocular clip implant. The ocular clip implant comprises an IOL-engaging portion at its distal end which comprises two opposing jaws, by way of illustration and not limitation, which are moveable with respect to each other in order to engage the IOL. It is to be noted that the ocular clip implant comprises jaws by way of illustration and that the IOL-engaging portion may comprise hooks or loops or any other engaging members.

It is to be noted that the IOL-engaging portion of the ocular clip implant grasps or otherwise engages or is configured to grasp or otherwise engage any part of an IOL. For some applications, the IOL-engaging portion grasps or otherwise engages or is configured to engage or otherwise grasp the optic of the IOL. For some applications, the IOL-engaging portion grasps or otherwise engages or is configured to engage or otherwise grasp the haptic(s) of the IOL. For some applications, the IOL-engaging portion grasps or otherwise engages or is configured to engage or otherwise grasp a capsule encapsulating the optic of the IOL. For some applications, the IOL-engaging portion grasps or otherwise engages or is configured to grasp or otherwise engage an anchor or separate fixation device which may have been anchored to any portion of the IOL prior to grasping of the IOL with the IOL-engaging portion.

For some applications, the IOL comprises a plate haptic lens, and the IOL-engaging portion grasps or otherwise engages or is configured to engage or otherwise grasp any portion of the plate haptic lens.

For some applications, the IOL-engaging portion of the ocular clip implant grasps or otherwise engages or is configured to engage or otherwise grasp tissue of the eye, e.g., the capsule, which has undergone fibrosis due to the presence of an IOL previously implanted in the eye. Movement of the ocular clip implant that grasps the tissue of the eye that has an IOL coupled thereto effects movement of the tissue of the eye, and thereby effects repositioning of the IOL coupled to the tissue.

Typically, the jaws have a tendency to close, and the introduction instrument controls movement of the opposing jaws so as to create negative space between the jaws so that a portion of the IOL (e.g., a portion of the optic, a portion of the haptic, or a portion of a capsule that encapsulates the optic of the IOL) can be positioned between the jaws. Once the IOL is positioned between the jaws, the jaws clamp onto and grasp the portion of the IOL. A similar method can also be used at a different side, such as at an opposing side, of the eye to engage a second portion of the IOL to further reposition the IOL.

For some applications, engaging the portion of the IOL comprises opening the IOL-engaging portion of the implant within the eye, moving the open IOL-engaging portion over the portion of the IOL, and allowing the jaws of the IOL-engaging portion to close in order to capture the portion of the IOL. Opening the engaging portion of the implant can include retracting an introduction sheath of the introduction instrument to uncover the jaws of the IOL-engaging portion. While in the sheath, the jaws are disposed in a first, generally straightened configuration. The introduction instrument comprises control shafts reversibly coupled to the implant which facilitate opening of the jaws by facilitating bending of the jaws. Once the jaws are allowed to close, a first jaw rests against and applies pressure to the upper surface of the portion of the IOL and the second jaw rests against and applies pressure to the lower surface of the portion of the IOL, such that the implant grasps the portion of the IOL.

The ocular clip implant comprises, at its proximal end, an ocular-wall-engaging portion configured to be anchored to native tissue of the ocular wall in order to fix the implant at its proximal end. That is, the implant comprises integrated first and second anchoring portions, i.e., the IOL-engaging portion and the ocular-wall-engaging portion, respectively. The ocular-wall-engaging portion is configured to anchor and fix the ocular clip implant to the eye (e.g., to the outer-most layer of the globe, such as to the sclera), such that the implant achieves fixation (and, optionally, repositioning prior to the fixation) of the IOL. During grasping of the portion of the IOL by the IOL-engaging portion, the ocular-wall-engaging portion is disposed in a straightened configuration with the introduction sheath of the introduction instrument. Once the IOL-engaging portion has grasped the portion of the IOL and facilitates repositioning of the IOL by the introduction instrument, the introduction instrument is moved proximally to position the ocular-wall-engaging portion at the entry point such that a part of the ocular-wall-engaging is disposed external to the eye. The introduction sheath is then retracted to expose the ocular-wall-engaging portion, and the ocular-wall-engaging portion assumes a shape which facilitates anchoring of the ocular-wall-engaging portion to the external surface of the eye. As such, the ocular clip implant has a singular unit comprising: (1) a portion that engages the IOL and functions as a forceps for grasping the IOL, integrated with (2) a portion that engages with and anchors the implant to native tissue of the eye, e.g., the external surface of the eye (e.g., sclera). In such a manner, the ocular clip implant facilitates fixation of the IOL without the need for sutures or bolsters.

In some applications of the present invention, anchoring of the ocular-wall-engaging portion is reversible such that the implant can be repositioned by the operating physician in order to achieve optimal positioning of the implant in order to achieve optimal fixation of the IOL. Unlike conventional techniques which typically fixate the repositioned lens using a suture, the ocular clip implant of the present invention is repositionable following the anchoring of the ocular clip implant to the wall of the eye. That is, after it is anchored, the ocular-wall-engaging portion can be released and disengaged from tissue in order to either reposition the ocular-wall-engaging portion and/or reposition the intraocular lens using the same entry point used by the introduction instrument.

Typically, in conventional techniques, the repositioning of the IOL is performed using a forceps tool introduced through one entry point into the eye, followed by using a suturing tool introduced through an additional entry point into the eye. In some conventional techniques, multiple entry points and exit points are used for delivery tools and/or forceps tools. Typically, suturing is performed to fixate the IOL, which requires at least two entry points. Unlike in these conventional techniques, the repositioning of the intraocular lens and anchoring to the wall of the eye of the ocular-wall-engaging portion of the ocular clip implant followed by removal of the tool used to perform the repositioning and anchoring of the present invention is performed using a single entry point into the eye through the sclera. As such, the present invention reduces the number of entry points to one, in particular because the ocular clip implant combines the functions of (1) the forceps which grasp the IOL and (2) the anchor which facilitates fixation of the implant to the wall of the eye. Thus, the present invention reduces the number of tools to a single tool, thereby eliminating the need for a forceps tool and a suture which requires entry and exit points in the eye at at least two separate points. Since the present invention does not use a suture to fixate the lens, the introduction instrument of the present invention facilitates (1) grasping of the IOL by the forceps function of the ocular clip implant, (2) optionally repositioning of the IOL by moving the ocular clip implant, and (3) anchoring the ocular clip implant to the wall of the eye.

Additionally, the combined forceps (to grasp the IOL) and anchor functionalities (to anchor the implant to the wall of the eye) of the ocular clip implant of the present invention provide a system in which a single introduction instrument is needed without the need for additional trocars and/or instruments. The forceps functionality of the implant enables the implant to grasp the IOL at any suitable location. Furthermore, the anchor functionality of the ocular clip implant provides a suture-less system to reposition and fixate the IOL thus obviating the task of suturing which is a technique requiring a level of skill.

It is to be noted that the ocular clip implant of the present invention corrects a full range of dislocation from partial or complete dislocation of the IOL as well as minor subluxation which may be caused by partial zonulolysis.

There is therefore provided, in accordance with some applications of the present invention, an ocular clip implant used for securing an intraocular lens (IOL) in an eye of a patient, the ocular clip implant including:

an IOL-engaging portion disposed at a first end of the ocular clip implant, the IOL-engaging portion being configured to grasp a portion of the IOL; and an ocular-wall-engaging portion integrated with and disposed at a second end of the ocular clip implant, the ocular-wall-engaging portion including an anchor transitionable from a first, straightened configuration to a second, non-straightened configuration to anchor the ocular clip implant to a wall of the eye in order to secure the IOL to the eye.

In some applications of the present invention, the ocular clip implant includes a superelastic material.

In some applications of the present invention, the ocular clip implant is rigid.

In some applications of the present invention, the anchor has a pointed tip configured to pierce the wall of the eye in order to secure the IOL to the eye.

In some applications of the present invention, the ocular-wall-engaging portion includes at least one hook transitionable from the straightened configuration to a curved configuration to anchor the ocular clip implant to the wall of the eye.

In some applications of the present invention, the ocular-wall-engaging portion is reversibly transitionable from the first, straightened configuration to the second, non-straightened configuration.

In some applications of the present invention, the ocular-wall-engaging portion includes a shape-memory material which transitions the ocular-wall-engaging portion from the first, straightened configuration to the second, non-straightened configuration, and the ocular-wall-engaging portion is deformable from the second, non-straightened configuration upon application of a force to the ocular-wall-engaging portion.

In some applications of the present invention, the ocular-wall-engaging portion is shaped so as to define an opening for reversible coupling of a suture to the ocular-wall-engaging portion, and application of a pulling force to the suture facilitates application of the force to the ocular-wall-engaging portion to deform the ocular-wall-engaging portion from the second configuration.

In some applications of the present invention, the IOL-engaging portion is configured to grasp an optic of the IOL.

In some applications of the present invention, the IOL-engaging portion is configured to grasp a haptic of the IOL.

In some applications of the present invention, the IOL-engaging portion includes first and second opposing jaws which are moveable with respect to each other to grasp the portion of the IOL, the first jaw being positionable against a first surface of the portion of the IOL at a first location to apply pressure to the first surface of the portion of the IOL, and the second jaw being positionable against a second surface of the portion of the IOL at the first location to apply pressure to the second surface of the portion of the IOL.

In some applications of the present invention, the ocular-wall-engaging portion includes a shape-memory material, and each one of the first and second jaws include a rigid material.

In some applications of the present invention, the first and second opposing jaws include shape-memory material, and the jaws are configured to assume a closed state in an absence of force applied thereto.

In some applications of the present invention, a system including the ocular clip implant the system further includes an introduction instrument including an introduction sheath configured to house and deliver the ocular clip implant, the ocular clip implant is disposed within the introduction sheath in a first, straightened configuration, and the ocular clip implant is deformable to a second, non-straightened configuration when exposed from within the introduction sheath.

In some applications of the present invention, the introduction instrument is configured to deliver the ocular clip implant through an entry point in the eye, facilitate grasping of the portion of the IOL by the IOL-engaging portion through the entry point, and facilitate anchoring of the ocular clip implant by the ocular-wall-engaging portion through the entry point.

In some applications of the present invention, the IOL-engaging portion includes first and second opposing jaws which are moveable with respect to each other to grasp the portion of the IOL, the first jaw being positionable against a first surface of the portion of the IOL at a first location to apply pressure to the first surface of the portion of the IOL, and the second jaw being positionable against a second surface of the portion of the IOL at the first location to apply pressure to the second surface of the portion of the IOL, and the introduction instrument includes at least one control shaft reversibly coupled to the ocular clip implant, and the at least one control shaft is moveable to control movement between the first and second opposing jaws.

In some applications of the present invention, the introduction instrument is reversibly coupled to the ocular-wall-engaging portion, and the introduction instrument is configured to deform the ocular-wall-engaging portion from the second configuration.

In some applications of the present invention, the introduction instrument includes at least one suture reversibly coupled to the ocular-wall-engaging portion, and application of a pulling force to the suture facilitates application of the force to the ocular-wall-engaging portion to deform the ocular-wall-engaging portion from the second configuration.

There is also provided, in accordance with some applications of the present invention, a method for securing an intraocular lens (IOL) in an eye of a patient, the method including:

introducing within the eye through an entry point in the eye an IOL-engaging portion of an ocular clip implant, the IOL-engaging portion disposed at a first end of the ocular clip implant;

grasping a portion of the IOL with the IOL-engaging portion;

securing the IOL to the eye by anchoring the ocular clip implant to a wall of the eye in by:

positioning an ocular-wall-engaging portion integrated with and disposed at a second end of the ocular clip implant, partially within the wall of the eye and through the entry point and partially proximally to the wall of the eye; and facilitating transitioning of the ocular-wall-engaging portion from a first, straightened configuration to a second, non-straightened configuration.

In some applications of the present invention, anchoring the ocular clip implant to the wall of the eye includes piercing the wall of the eye with an anchor of the ocular-wall-engaging portion.

In some applications of the present invention, grasping the portion of the IOL includes grasping an optic of the IOL by the IOL-engaging portion.

In some applications of the present invention, grasping the portion of the IOL includes grasping a haptic of the IOL by the IOL-engaging portion.

In some applications of the present invention, grasping the portion of the IOL with the IOL-engaging portion includes:

moving first and second opposing jaws of the IOL-engaging portion with respect to each other, and by the moving:

positioning the first jaw being against a first surface of the portion of the IOL at a first location;

positioning the second jaw being against a second surface of the portion of the IOL at the first location; and applying pressure to the first and the second surfaces of the portion of the IOL by the first and the second jaws, respectively.

In some applications of the present invention, the method further includes, subsequently to the grasping, repositioning the IOL within the eye by moving the IOL with the IOL-engaging portion grasped thereto.

In some applications of the present invention, anchoring the ocular clip implant includes reversibly anchoring the ocular clip implant by applying a force to the ocular-wall-engaging portion.

In some applications of the present invention, applying the force to the ocular-wall-engaging portion includes applying a pulling force to the ocular-wall-engaging portion by pulling a suture reversibly coupled to the ocular-wall-engaging portion.

In some applications of the present invention, applying the force to the ocular-wall-engaging portion includes deforming the ocular-wall-engaging portion from the second, non-straightened configuration to the first, straightened configuration.

In some applications of the present invention, the method further includes:

further repositioning the IOL coupled to IOL-engaging portion the via the entry point subsequently to the deforming the ocular-wall-engaging portion; and subsequently, re-anchoring the ocular clip implant to the wall of the eye by:

repositioning the ocular-wall-engaging portion partially within the wall of the eye and through the entry point and partially proximally to the wall of the eye; and facilitating transitioning of the ocular-wall-engaging portion from the first, straightened configuration to the second, non-straightened configuration.

In some applications of the present invention, introducing the IOL-engaging portion includes introducing at least a portion of an introduction instrument housing the ocular clip implant through the entry point, further repositioning the IOL includes using the introduction instrument to move the IOL-engaging portion coupled to the portion of the IOL via the entry point, and re-anchoring the ocular clip implant includes using the introduction instrument to re-anchor the ocular clip implant via the entry point.

The present invention will be more fully understood from the following detailed description of embodiments thereof, taken together with the drawings, in which:

DETAILED DESCRIPTION OF APPLICATIONS

Figure 1A:
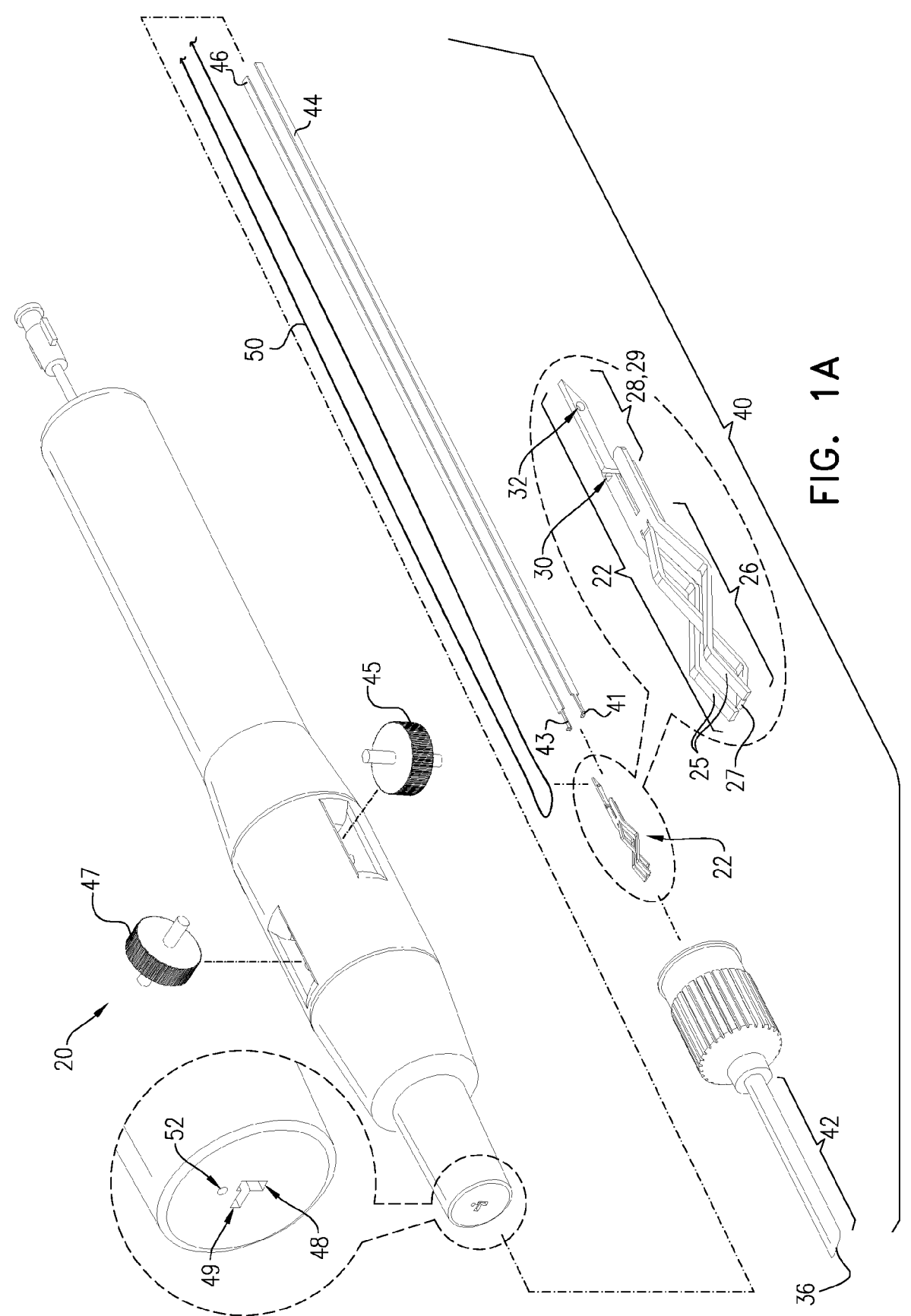
FIGS. 1A-B and 2 are schematic illustrations of examples of a system comprising an introduction instrument configured for delivering an ocular clip implant, in accordance with some applications of the present invention.
Figure 1B:
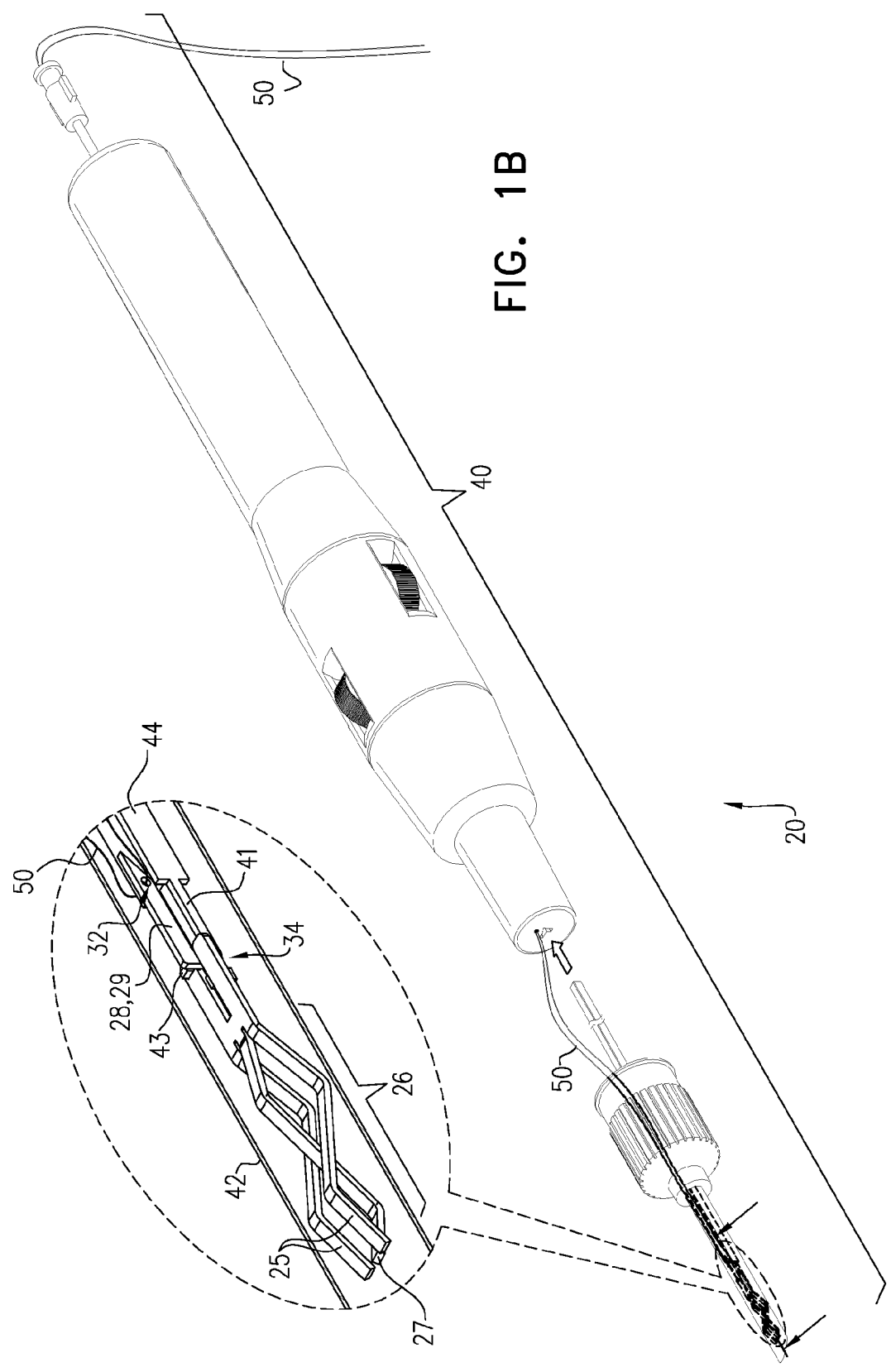
Figure 2:
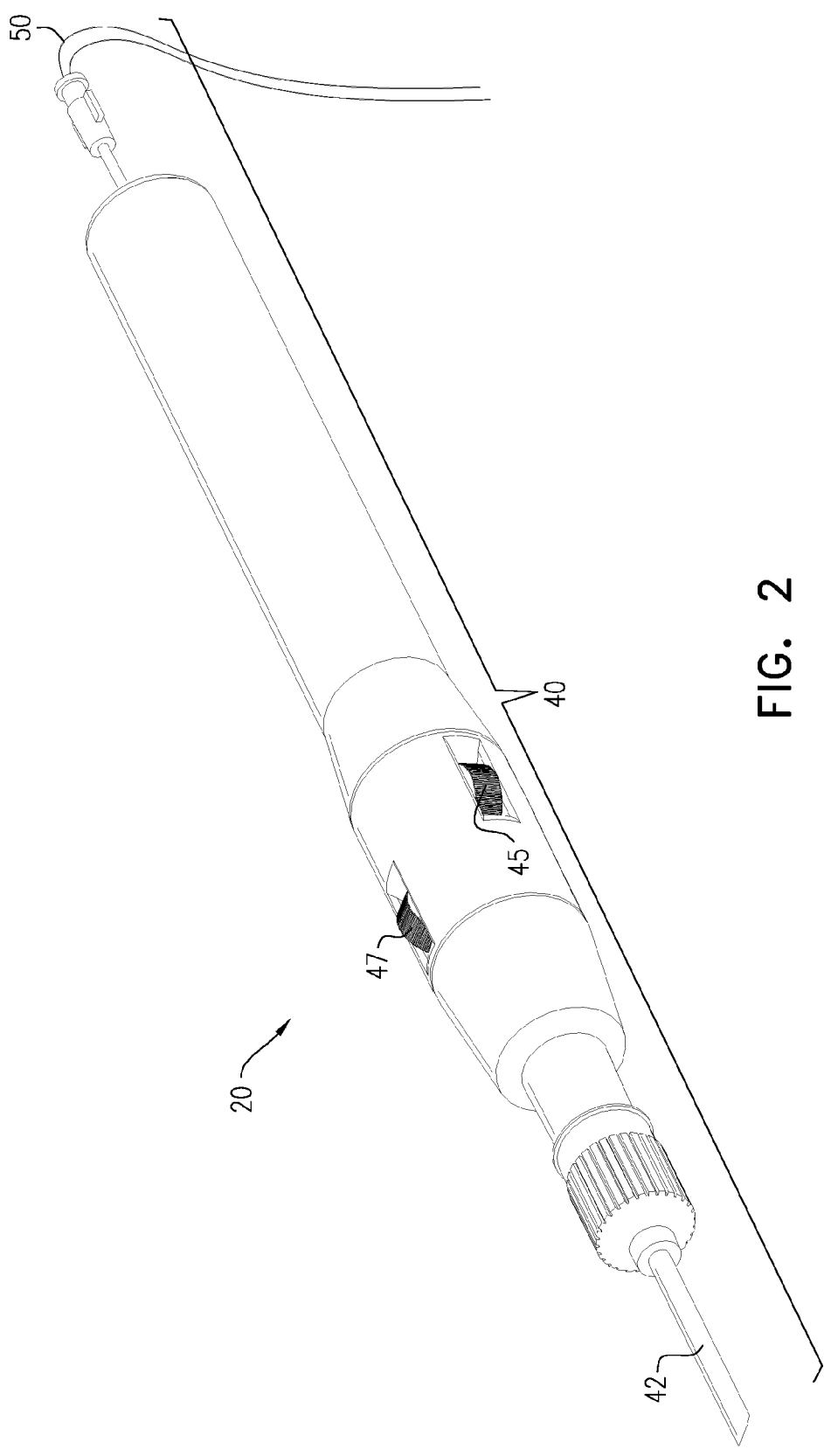

Reference is now made to FIGS. 1A-B and 2, which are schematic illustrations of a system 20 comprising an implantable device comprising an ocular clip implant 22 used to secure and optionally to reposition an intraocular lens (IOL) 62, in accordance with some applications of the present invention. Ocular clip implant 22 comprises an IOL-engaging portion 26 at a first end of ocular clip implant 22 and an ocular-wall-engaging portion 28 integrated with and at a second end of implant 22. For some applications, IOL-engaging portion 26 and an ocular-wall-engaging portion 28 are fabricated from a single piece. Typically, IOL 62 is not an element of system 20.

Instrument 40 is shown in its assembled state in FIG. 2.

(It is to be noted that in the context of the specification and the claims, the term "clip" means grab or grasp and does not mean cut. The term "ocular clip implant" may also be expressed as "ocular fixation implant.")

IOL-engaging portion 26 comprises first and second opposing jaws 25 and 27, which are moveable with respect to each other to grasp or otherwise engage IOL 62, such as an optic 61 of IOL 62, a haptic of IOL 62, or a capsule encapsulating the optic of the IOL. (In the context of the present application, as per common usage in the art, an "IOL" comprises an optic, also known as the lens, and, optionally, one or more haptics for holding the optic in place in the capsular bag inside the eye.) It is to be noted that although system 20 is generally described herein as grasping or being configured to grasp optic 61 of IOL 62, system 20 may also be configured to grasp the haptic(s) of IOL 62, mutatis mutandis. For some applications, IOL-engaging portion 26 grasps or is configured grasp an anchor which may be anchored to any portion of the IOL prior to grasping of the IOL with IOL-engaging portion 26. While FIGS. 4A-5C show implant 22 grasping optic 61 of IOL 62, and FIG. 6 shows implant 22 grasping a haptic 67 of an IOL 68, it is to be noted that implant 22 may grasp or otherwise engage (1) any portion of the IOL, included but not limited to: (a) the optic, (b) the haptic, and/or (c) a capsule encapsulating the optic, and/or (2) any portion of an anchor, a fixation device, or any other device previously coupled to the IOL, e.g., such as during a previous procedure.

For some applications, the IOL comprises a plate haptic lens, and IOL-engaging portion 26 grasps or otherwise engages or is configured to engage or otherwise grasp any portion of the plate haptic lens.

It is to be noted that ocular clip implant 22 comprises jaws 25 and 27 by way of illustration, and that IOL-engaging portion 26 may comprise hooks or loops or any other engaging members.

First jaw 25 is positionable against a first surface of optic 61 at a first location to apply pressure to the first surface of optic 61. Second jaw 27 is positionable against a second surface of optic 61 at the first location to apply pressure to the second surface of optic 61. For some applications, first and second jaws 25 and 27 have a tendency to close and are configured to assume a closed state in an absence of force applied to jaws 25 and 27 (i.e., in a resting state), and movement between (e.g., the opening of) jaws 25 and 27 is facilitated by an introduction instrument 40 used to deliver ocular clip implant 22, as is described hereinbelow. For some applications, each of jaws 25 and 27 comprises a rigid material, and jaws 25 and 27 are coupled together by a hinge. For some applications, each of jaws 25 and 27 comprises a superelastic material. e.g., nitinol. For some applications, each of jaws 25 and 27 comprises a material having shape-memory, e.g., nitinol. For some applications, jaws 25 and 27 are fabricated from a single piece.

Typically, implant 22 comprises a biocompatible material. For some applications, implant 22 comprises a superelastic material, e.g., nitinol. For some applications, implant 22 comprises a rigid material. For some applications, implant 22 comprises a metal, e.g., stainless steel, titanium or nitinol.

Ocular-wall-engaging portion 28 is integrated with ocular clip implant 22 and comprises an anchor 29 that is transitionable from a first, straightened configuration (as shown in FIGS. 1A-B) to a second configuration (shown in FIGS. 4F-H hereinbelow) in order to anchor ocular clip implant 22 to a wall of the eye, e.g., the sclera of the eye, as is described hereinbelow.

Figure 4A:
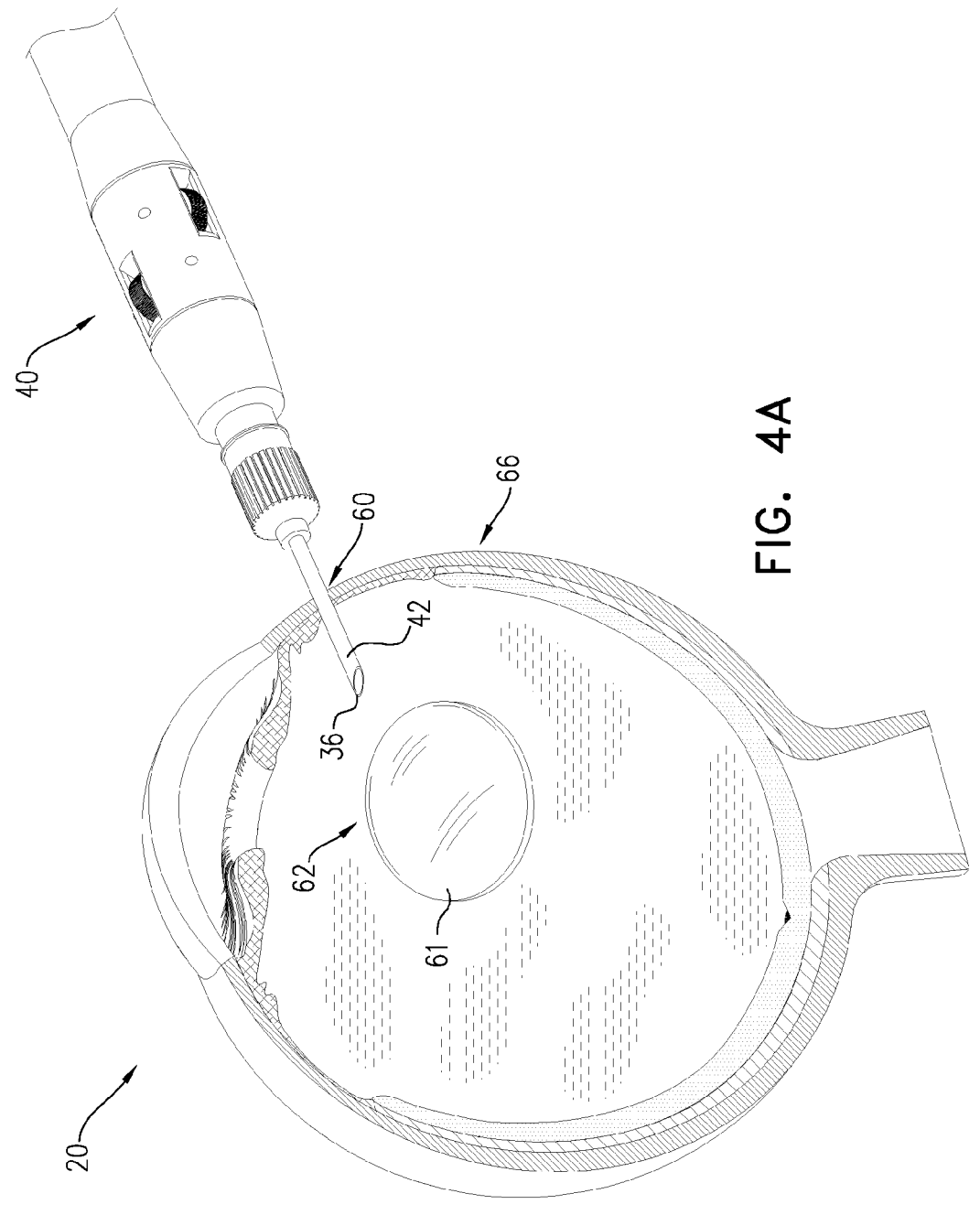
Figure 4B:
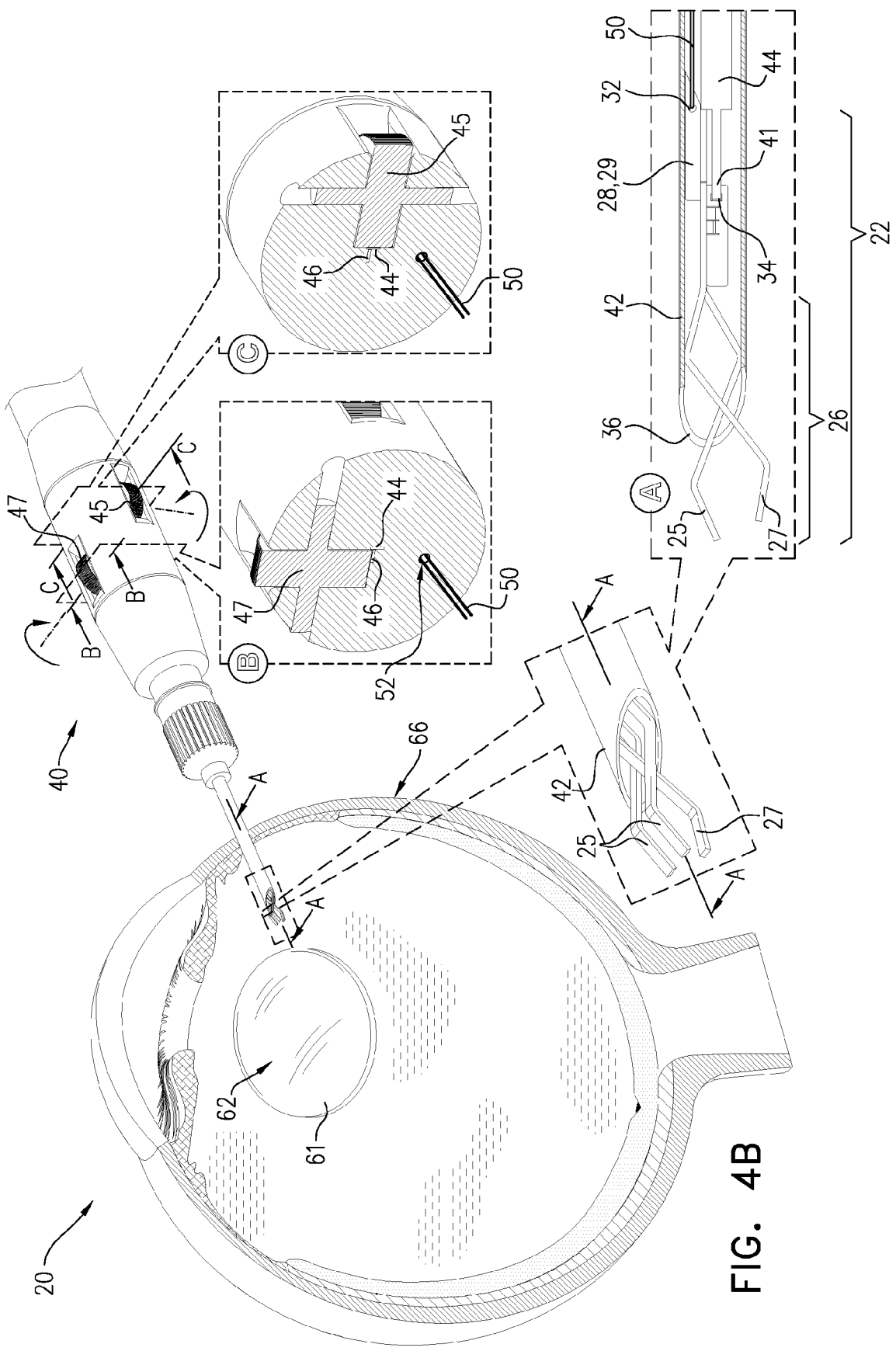

System 20 comprises an introduction instrument 40, which comprises a device having a handle portion and a distal introduction sheath 42, which houses ocular clip implant 22 during delivery of implant 22 into the eye. Introduction sheath 42 comprises a metal, e.g., stainless steel, titanium or nitinol. Introduction sheath 42 is shaped so as to define a pointed or beveled distal tip 36 that is configured to penetrate the eye in order to facilitate delivery of implant 22 into the eye. Introduction sheath 42 is shaped so as to define a lumen which houses implant 22 in a generally elongated and straightened delivery configuration. Introduction sheath 42 is configured to house and deliver ocular clip implant 22 while ocular clip implant 22 is disposed within introduction sheath 42 in a first, straightened configuration, such as shown in FIGS. 1A-B. Ocular clip implant 22 is deformable to a second, non-straightened configuration when exposed from within introduction sheath 42, such as shown in FIG. 4B.

As shown by way of illustration and not limitation, jaw 25 comprises two tines and jaw 27 comprises one tine. It is to be noted that each of jaws 25 and 27 may comprise any suitable number of tines. For some applications, jaws 25 and 27 may each comprise a plate (configuration not shown). For some application, jaws 25 and 27 have textured, ridged, or serrated surfaces which increases friction between IOL-engaging portion 26 and optic 61 of IOL 62.

Alternatively, for some applications, jaws 25 and 27 are elastic and have a tendency to open and are configured to assume an opened state in an absence of force applied to jaws 25 and 27, and movement between (e.g., the closing of) jaws 25 and 27 is controlled by control shafts 44 and 46 to help close jaws 25 and 27. Sheath 42 additionally maintains jaws 25 and 27 in the closed state.

Typically, introduction instrument 40 controls the opening and closing of jaws 25 and 27 of IOL-engaging portion 26. Implant 22 is shaped so as to define openings 30 and 34 in proximity to jaws 25 and 27. Instrument 40 comprises control shafts 44 and 46 which are reversibly coupled to implant 22 via openings 30 and 34. For some applications, a single shaft combines the functions of shafts 44 and 46. Shaft 44 comprises a hook 41 at a distal end of shaft 44 which engages with opening 34 of implant 22, and shaft 46 comprises a hook 43 which engages with opening 30 (shown in FIG. 1A) of implant 22. Shafts 44 and 46 comprise elongate rectangular shafts, e.g., bands or ribbons, which are disposed perpendicularly with respect to each other in respective lumens 48 and 49 of instrument 40. For some applications, shafts 44 and 46 comprise cylindrical shafts. Shafts 44 and 46 comprise a metal, silicone, or plastic. Instrument 40 comprises control knobs 45 and 47 which engage respective control shafts 44 and 46 by pressing against and applying pressure to shafts 44 and 46, as is described hereinbelow with reference to FIG. 4B.

For some applications, shafts 44 and 46 are not movable independently of each other, as shown, but rather, shafts 44 and 46 are combined into a single, unitary shaft.

It is to be noted that the handle of instrument 40 comprises knobs 45 and 47 and shafts 44 and 46 by way of illustration and not limitation. Control of implant 22 may be provided by any mechanism other than knobs 45 and 47 and shafts 44 and 46.

Reference is now made to FIG. 4B. As shown in View B, knob 47 presses against and rotates against the flat surface of control shaft 46. Rotation of knob 47 in a first rotational direction applies pressure to shaft 46 which moves shaft 46 and hook 43 of shaft 46 in a first linear direction which facilitates movement of jaw 25 and/or jaw 27 since hook 43 of shaft 46 is reversibly coupled to implant 22 via opening 34 of implant 22. As shown in View C, knob 45 presses against and rotates against the flat surface of control shaft 44. Rotation of knob 45 in a first rotational direction applies pressure to shaft 44 which moves shaft 44 and hook 41 of shaft 44 in a first linear direction which facilitates movement of jaw 27 and/or jaw 25 since hook 41 of shaft 44 is reversibly coupled to implant 22 via opening 34 of implant 22. Conversely, rotation of knobs 45 and 47 in the opposite second direction facilitates movement of shafts 44 and 46, respectively, in the opposite second linear direction. In order to achieve the most efficient opening and/or closing of jaws 25 and 27, knobs 45 and 47 are moved in any suitable direction together and interchangeably. Movement of knobs 45 and 47 creates application of pressure to jaws 25 and 27 in order to facilitate proper opening and/or closing of jaws 25 and 27. As such, instrument 40 provides control of the opening and/or closing jaws 25 and 27 of IOL-engaging portion 26 by knobs 45 and 47. Jaws 25 and 27 of IOL-engaging portion 26 function as forceps, i.e., graspers, which grasp optic 61 of IOL 62 at any suitable location along optic 61 in order to facilitate manipulation of IOL 62.

For applications in which jaws 25 and 27 have a tendency to close, movement of control knobs 45 and 47 facilitate mechanical opening of jaws 25 and 27 so that jaws 25 and 27 may be positioned appropriately with respect to a portion of IOL 62 in a manner in which the portion of IOL 62 is fitted between jaws 25 and 27. Once jaws 25 and 27 are in alignment with IOL 62, jaws 25 and 27 are allowed to close, e.g., by removing forces applied to jaws 25 and 27 and/or by moving knobs 45 and 47 in the opposite direction to the direction knobs 45 and 47 are rotated during opening of jaws 25 and 27. Once IOL-engaging portion 26 assumes the closed state, jaw 25 is positioned against and applies pressure to an upper surface of IOL 62 and jaw 27 is positioned against and applies pressure to a lower surface of IOL 62. In such a manner, IOL-engaging portion 26 of implant 22 functions as forceps, i.e., graspers, which grasp IOL 62.

Reference is again made to FIGS. 1A-B and 2. Implant 22 comprises ocular-wall-engaging portion 28 which is configured to engage native tissue of the eye in order to fixate implant 22 and prevent movement of IOL 62 once implant 22 grasps onto IOL 62 and is used to reposition and center IOL 62. Ocular-wall-engaging portion 28 comprises a biocompatible material. For some applications, portion 28 comprises a superelastic material, e.g., nitinol. For some applications, implant 22 comprises a metal, e.g., stainless steel, titanium or nitinol. Ocular-wall-engaging portion 28 of implant 22 is disposed typically opposite. e.g., at a second end of implant 22, IOL-engaging portion 26, which is disposed at a first end of implant 22.

As shown in FIGS. 1A-B, ocular-wall-engaging portion 28 is disposed in a straightened configuration when portion 28 is disposed within the lumen of introduction sheath 42. Since ocular-wall-engaging portion 28 comprises a material having shape-memory, once ocular-wall-engaging portion 28 is exposed from within sheath 42, ocular-wall-engaging portion 28 transitions to a second, non-straightened configuration in order to anchor implant 22 to the wall of the eye, as described hereinbelow. For some applications, ocular-wall-engaging portion 28 comprises at least one hook transitionable from the straightened configuration to a curved configuration in order to anchor implant 22 to the wall of the eye. Typically, ocular-wall-engaging portion 28 provides anchoring of implant 22 to the wall of the eye when in the second, non-straightened configuration and does not provide anchoring of implant 22 to the wall when in the first, generally straightened configuration.

Although ocular-wall-engaging portion 28 has a tendency to assume the second, non-straightened configuration in the absence of a force applied thereto, the transitioning of portion 28 from the straightened configuration to a non-straightened configuration is reversible, e.g., by applying a force to portion 28 in order to reshape and deform portion 28 from its second configuration. Ocular-wall-engaging portion 28 is shaped so as to define an opening 32 for passage therethrough of at least one suture 50 to ocular-wall-engaging portion 28. Opening 32 provides reversible coupling of suture 50 to ocular-wall-engaging portion 28. For some applications, a wire is coupled to ocular-wall-engaging portion 28 in place of suture 50. Application of a pulling force to suture 50 facilitates application of the force to ocular-wall-engaging portion 28 to deform ocular-wall-engaging portion 28 from the second configuration into a different shape, e.g., back into the straightened configuration. Suture 50 is looped through opening 32 of ocular-wall-engaging portion 28 and extends through a lumen 52 within instrument 40. Suture 50 is exposed out of a proximal end of instrument 40 such that the physician may apply forces to one or both ends of sutures in order to reshape ocular-wall-engaging portion 28 once ocular-wall-engaging portion 28 is exposed from within introduction sheath 42. Once ocular-wall-engaging portion 28 is appropriately positioned with respect to the native tissue of the eye, suture 50 is decoupled from ocular-wall-engaging portion 28 by pulling on one end of suture 50.

For some applications, suture 50 comprises a metal, silicone, or plastic suture material, e.g., nylon or prolene. For some applications, system 20 does not comprise suture 50, but rather system 20 comprises a different mechanism or shaft within instrument 40 which applies force to ocular-wall-engaging portion 28 to deform ocular-wall-engaging portion 28.

Reference is now made to FIGS. 3 and 4A-H, which are schematic illustrations of a method using system 20 for repositioning and securing the dislocated IOL 62 by advancing introduction instrument 40 housing implant 22 to IOL 62 anterior to the vitreous, fastening implant 22 to IOL 62, moving the IOL to a centered position within the eye using implant 22, and fastening implant 22 to the wall of the eye, in accordance with some applications of the present invention.

System 20 is configured to correct subluxation, or dislocation, of IOL 62. For some applications, system 20 is configured to correct decentration, which may be in any direction such as temporal, nasal, superior or inferior. For some applications, system 20 is configured to correct posterior dislocation of the IOL into the vitreous. In such applications, system 20 is configured to lift the IOL forward from the vitreous into the ciliary sulcus. For some applications, system 20 is configured to correct posterior dislocation of the IOL into the anterior vitreous. For some applications, system 20 is configured to correct dislocation of the IOL during a vitrectomy.

Figure 3:
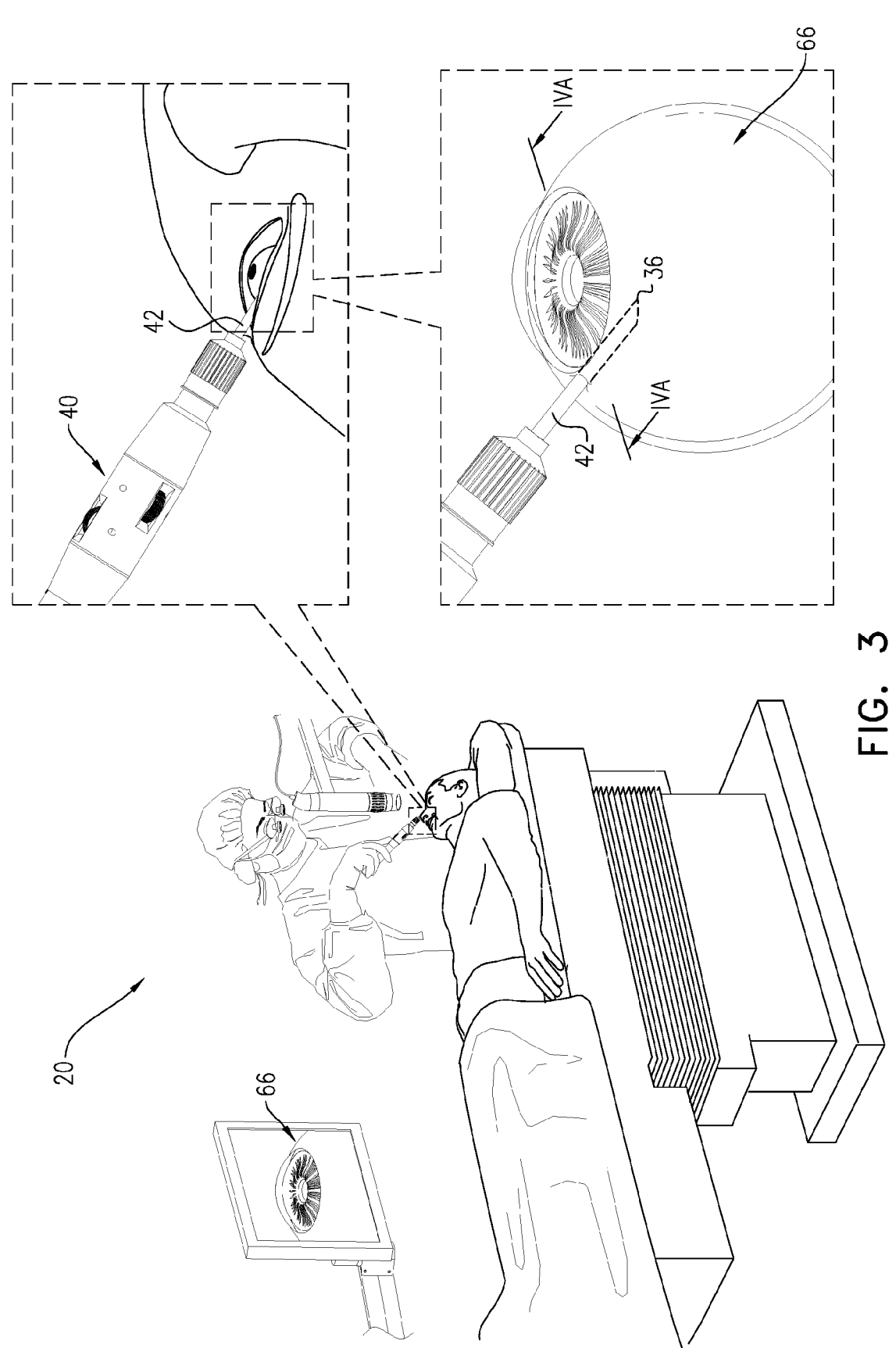
FIGS. 3 and 4A-H are schematic illustrations of examples of a method for using the introduction instrument of FIGS. 1A-B and 2 in order to implant the ocular clip implant for fixation of an intraocular lens (IOL), in accordance with some applications of the present invention.

As shown in FIG. 3, a distal portion of instrument 40, e.g., introducer sheath 42, is advanced into eye 66 through a single entry point 60, e.g., without the need for additional entry points for other instruments. Typically, pointed distal tip 36 creates entry point 60 (as shown in FIG. 4A) in the wall of the eye. System 20 comprises ocular clip implant 22 which comprises an integrated first and second anchoring portions, i.e., (1) IOL-engaging portion 26 which act as forceps and graspers to grasp IOL 62, and (2) ocular-wall-engaging portion 28 which comprises anchor 29 which anchors implant 22 to native tissue of eye 66 and thereby fixates IOL 62 after repositioning. As a result, system 20 requires a single entry point 60 without the need for additional entry points. During the positioning of sheath 42 into eye 66, the operating physician holds the handle portion of instrument 40 in a position outside of the sclera. As shown in FIG. 4A, instrument 40 is advanced through the wall of eye 66, exterior to the ciliary sulcus and toward IOL 62 which is disposed posteriorly, in the vitreous. Instrument 40 is advanced in a manner in which introduction sheath 42 is positioned close to IOL 62. Introduction sheath 42 holds within it implant 22 in a compressed and closed delivery state.

As shown in FIG. 4B, a distal portion, e.g., a portion of IOL-engaging portion 26 is gradually pushed distally out of sheath 42 such that jaws 25 and 27 are exposed from within sheath 42. For some applications, jaws 25 and 27 are exposed from within sheath 42 by pushing on implant 22 distally by one or more of shafts 44 and 46. Jaws 25 and 27 are exposed from within sheath 42 by retracting sheath 42 with respect to implant 22.

As described hereinabove, once the distal portions of jaws 25 and 27 are exposed from within sheath, knobs 45 and 47 are rotated so that they press against respective control shafts 44 and 46. Since shafts 44 and 46 are coupled to ocular clip implant 22, as described hereinabove, movement of shafts 44 and 46 applies pressure to and controls movement between jaws 25 and 27. Typically, jaws 25 and 27 have a tendency to close. Movement of shafts 44 and 46 in such embodiments controls opening jaws 25 and 27 such that a negative space is created between jaws 25 and 27 for fitting within the negative space of a portion of optic 61 of IOL 62. For some applications, jaws 25 and 27 instead engage a haptic of IOL 62 or are shaped and configured to engage a haptic of IOL 62.

Figure 4C:
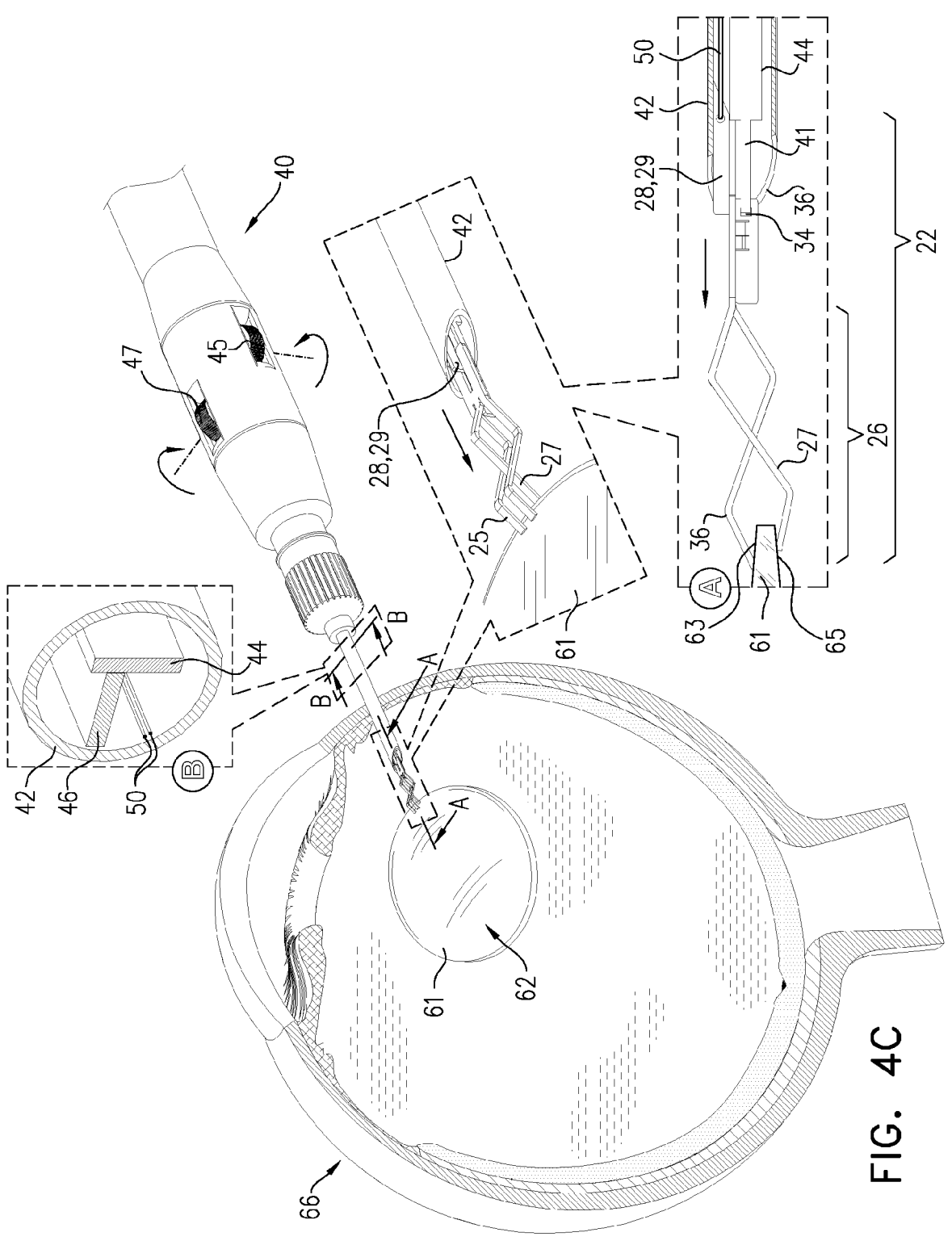

As shown in FIG. 4C, once jaws 25 and 27 are in the opened state, instrument 40 is maneuvered such that the portion of optic 61 of IOL 62 fits in the negative space between jaws 25 and 27. Jaws 25 and 27 are either allowed to close, as they have a tendency to assume the closed position, and/or shafts 44 and 46 are moved in the direction opposite to the direction they were moved in order to facilitate opening of jaws 25 and 27. Movement of shafts 44 and 46 in the opposite direction is controlled by movement of knobs 45 and 47 in the direction opposite to the direction they were moved in order to facilitate opening of jaws 25 and 27. In the closed state of IOL-engaging portion 26, jaw 25 is positioned at and applies pressure to a first surface 63 (e.g., an upper surface) of a portion of optic 61 of IOL 62 at a first location, and jaw 27 is positioned at and applies pressure to a second surface 65 (e.g., a lower surface) of the portion of optic 61 of IOL 62 at the first location. Thus, the portion of optic 61 of IOL 62 is sandwiched between jaws 25 and 27 in the closed state of IOL-engaging portion 26. As such, IOL-engaging portion 26 of ocular clip implant 22 functions as forceps, or graspers, which grasp IOL 62. Once ocular clip implant 22 grasps IOL 62, movement and repositioning of IOL 62 into the appropriate position with respect to the native eye by instrument 40 via IOL-engaging portion 26 of ocular clip implant 22 is achieved, as shown in FIG. 4D.

For some applications, since jaws 25 and 27 have a tendency to close, the force between jaws 25 and 27 is sufficient to maintain coupling of IOL-engaging portion 26 to optic 61 of IOL 62 in a manner in which implant 22 functions a permanent fixation clip. Alternatively or additionally, jaws 25 and 27 may be further permanently locked in place with respect to IOL 62 by a locking mechanism, e.g., a crimping mechanism or a cinching mechanism. For some applications, a cinch lock is pushed distally from a proximal portion of implant 22, compressing jaws 25 and 27 to close further. The cinch lock may be locked in place, e.g., by engaging a groove on the exterior surface of implant 22. The groove functions as a stopper, preventing the clinch lock from moving beyond the groove. It is to be noted that, for some application, the locking mechanism which locks in place jaws 25 and 27 is engaged after proper positioning of IOL 62 in the appropriate location.

Figure 4D:
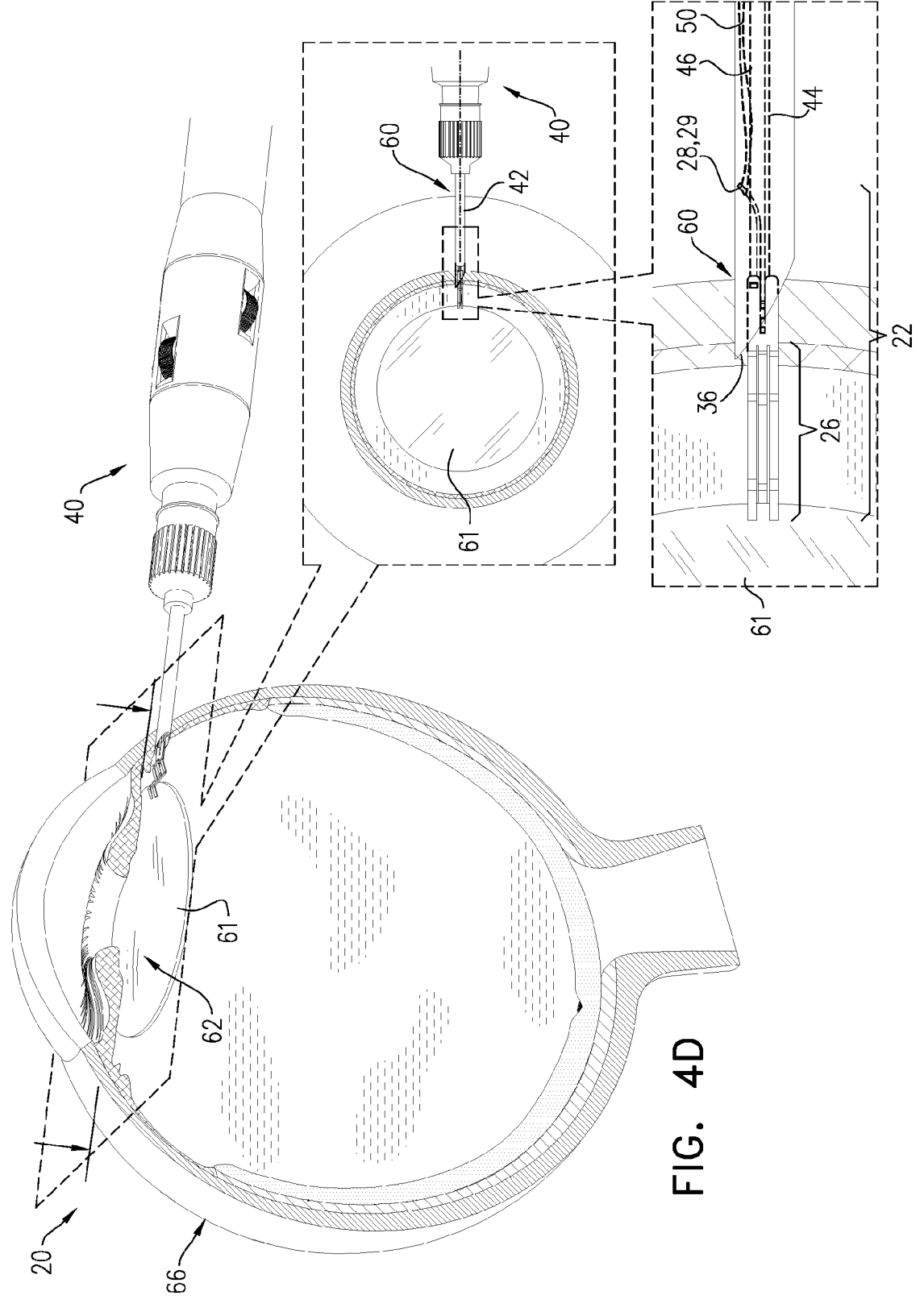

As shown in FIG. 4D, system 20 may be used to mobilize the dislocated IOL 62 inside eye 66 in any direction since IOL-engaging portion 26 of implant 22 operates as forceps, i.e., graspers. IOL-engaging portion 26 also functions as a fastener of implant 22 to IOL 62.

During the grasping of IOL 62 by IOL-engaging portion 26, anchor 29 of ocular-wall-engaging portion 28 remains in the first, generally-straightened, or straightened, configuration within the lumen of introduction sheath 42, as shown in FIG. 4D. Sheath 42 protects wall 64 of eye 66 and prevents inadvertent or premature engagement of anchor 29 with native tissue of eye 66. That is, only once (1) IOL-engaging portion 26 grasps and fastens to IOL 62, and (2) IOL 62 is properly repositioned, then, as described hereinbelow, instrument 40 is retracted through the entry point 60 so as to position (i) a distal portion of ocular-wall-engaging portion 28 within and through entry point 60 and (ii) a proximal portion of ocular-wall-engaging portion 28 proximally to the wall of eye 66, e.g., proximally to wall 64. As such, anchor 29 is positioned partially within wall 64 and partially proximally to wall 64 so that the proximal portion of anchor 29 can be anchored to the wall of eye 66.

For some applications of the present invention, instrument 40 comprises a safety which prevents premature retraction of sheath 42 and/or deployment of implant 22 from within sheath 42. For some applications, instrument comprises a stop which is operable by the operating physician. For some applications, one or more of knobs 45 and 47 prevents retracting of sheath 42 prematurely and/or prevents premature overexposing of ocular-wall-engaging portion 28 of implant 22 from within sheath 42.

During grasping and repositioning of IOL 62 as well as retracting of instrument 40 through wall 64 at entry point 60, suture 50 remains coupled ocular-wall-engaging portion 28.

Figure 4E:
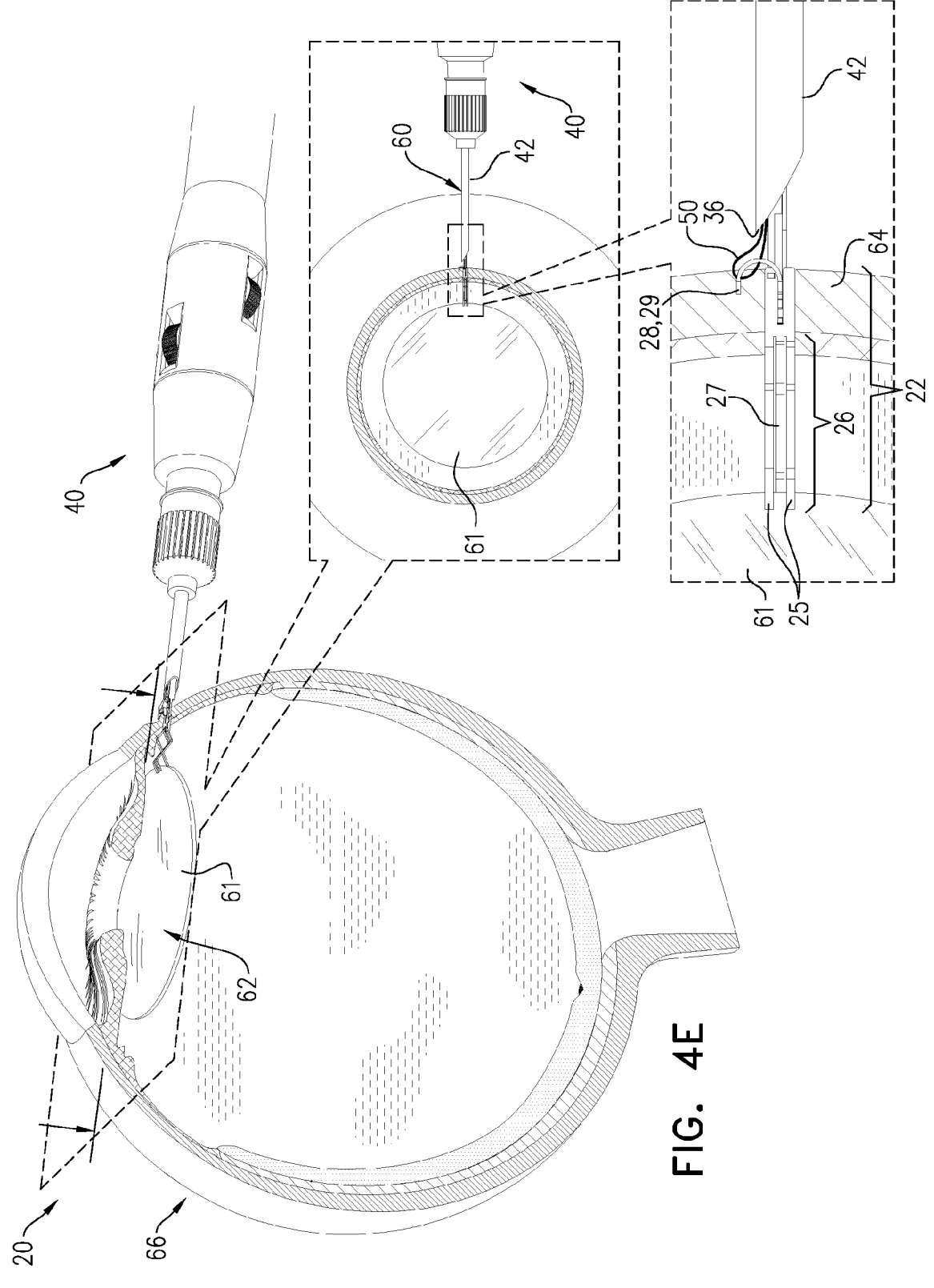
Figure 4F:
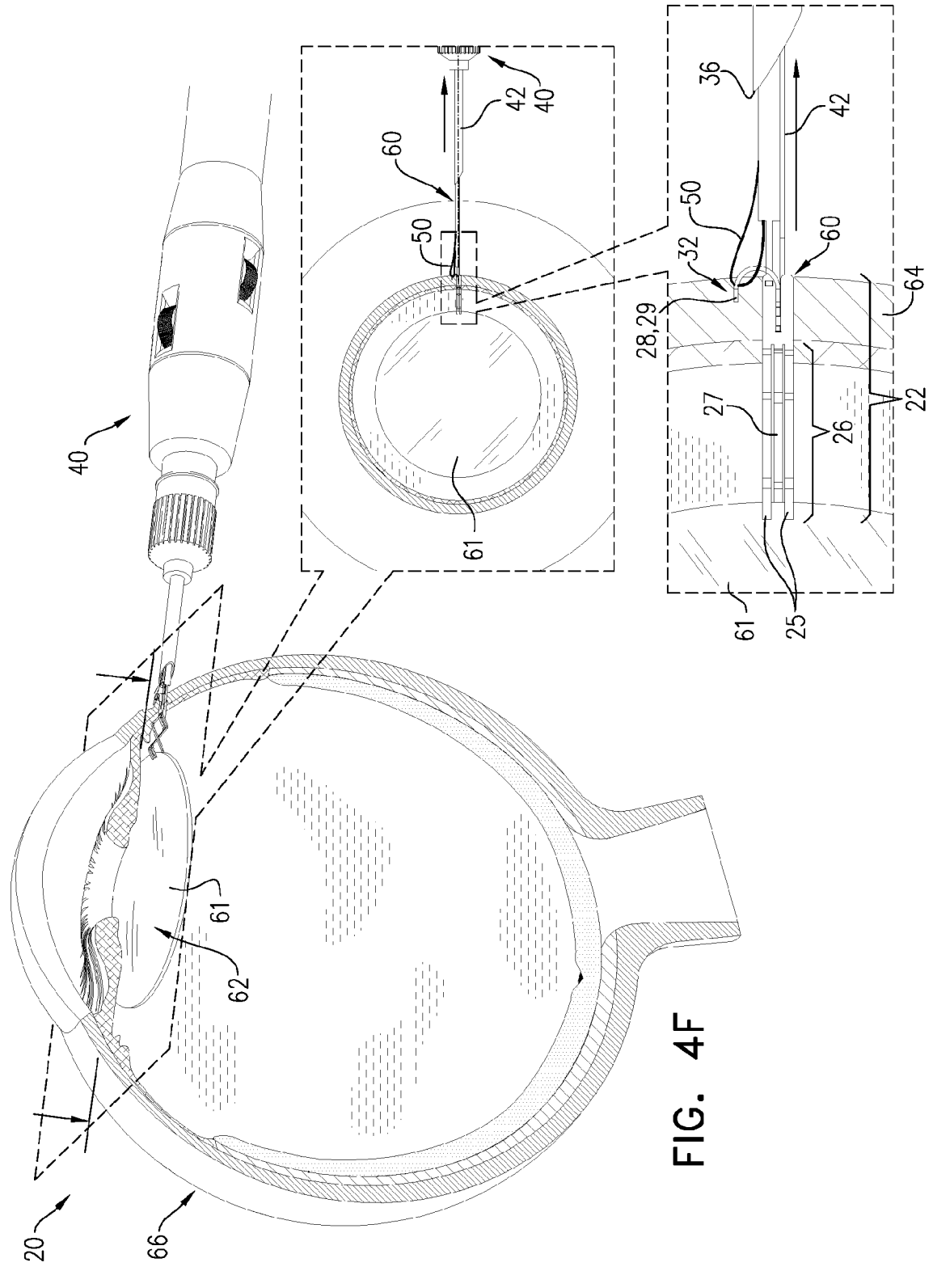

FIG. 4E shows deployment of ocular-wall-engaging portion 28 from within sheath 42 by either distally pushing implant 22 from within sheath 42 and/or retracting sheath 42 proximally. Anchor 29 of ocular-wall-engaging portion 28 is positioned partially within the wall of the eye and through entry point 60 and positioned partially proximally to the wall of eye 66, e.g., proximally to wall 64. Positioning the proximal portion of ocular-wall-engaging portion 28 proximally to the wall of the eye, facilitates transitioning of ocular-wall-engaging portion 28 from the first, straightened configuration to the second, non-straightened configuration. Once anchor 29 of ocular-wall-engaging portion 28 is exposed from within sheath 42, anchor 29 transitions from the first, straightened configuration to the second non-straightened configuration because anchor 29 comprises a shape-memory material. e.g., nitinol, which a tendency to assume the non-straightened configuration. As shown, anchor 29 comprises a hook which has a tendency to assume the curved configuration, as shown in FIGS. 4E-F. Anchor 29 has a pointed tip configured to pierce wall 64 of the eye, in order to secure IOL 62 to eye 66.

For some applications, anchor 29 may comprise any suitable number of hooks, e.g., two. It is to be noted that anchor 29 may assume any suitable shape. Once transitioned to the second, non-straightened configuration, ocular-wall-engaging portion 28 engages with the wall 64. It is to be noted that ocular-wall-engaging portion 28 may comprise more than one anchor 29, e.g., two or three or any suitable number of anchors 29.

In all applications of the present invention, ocular-wall-engaging portion 28 provides a suture-less coupling of implant 22 to wall 64 of eye 66 or to the sclera. In other words, ocular clip implant 22, by comprising anchor 29 of ocular-wall-engaging portion 28, is capable of grasping IOL 62 using the forceps feature of IOL-engaging portion 26, facilitate optional repositioning of IOL 62 while grasping IOL 62, and facilitate fixation on IOL 62 after optional repositioning without the need for sutures and/or any additional instruments or any additional entry points into eye 66.

Once anchor 29 is anchored to wall 64 of eye 66, sheath 42 may be retracted by retracting instrument 40, as shown in FIG. 4F.

For some applications, a length of implant 22 is preselected in advance of the repositioning procedure. For some applications, a total length of implant 22 is adjustable in situ using an adjustment mechanism, e.g., a ratchet mechanism, coupled to implant 22. For such applications, for example, IOL-engaging portion 26 and ocular-wall-engaging portion 28 comprise two separate pieces that are coupled together by the adjustment mechanism.

Anchoring of ocular-wall-engaging portion 28 to wall 64 of the eye prevents tilting, rotating, swiveling, or otherwise displacing of IOL 62 following the repositioning of IOL 62.

Before instrument 40 is disengaged from implant 22, the operating physician checks to see whether ocular-wall-engaging portion 28 has successfully anchored to wall 64 or to the sclera and checks to see if IOL 62 is properly repositioned. If the physician finds that either IOL 62 or anchor 29 is not appropriately positioned, system 20 provides a mechanism by which anchoring of ocular-wall-engaging portion 28 is reversible so that the physician can either reposition anchor 29 and, if necessary, also further reposition IOL 62 before deploying anchor 29 again.

Figure 4G:
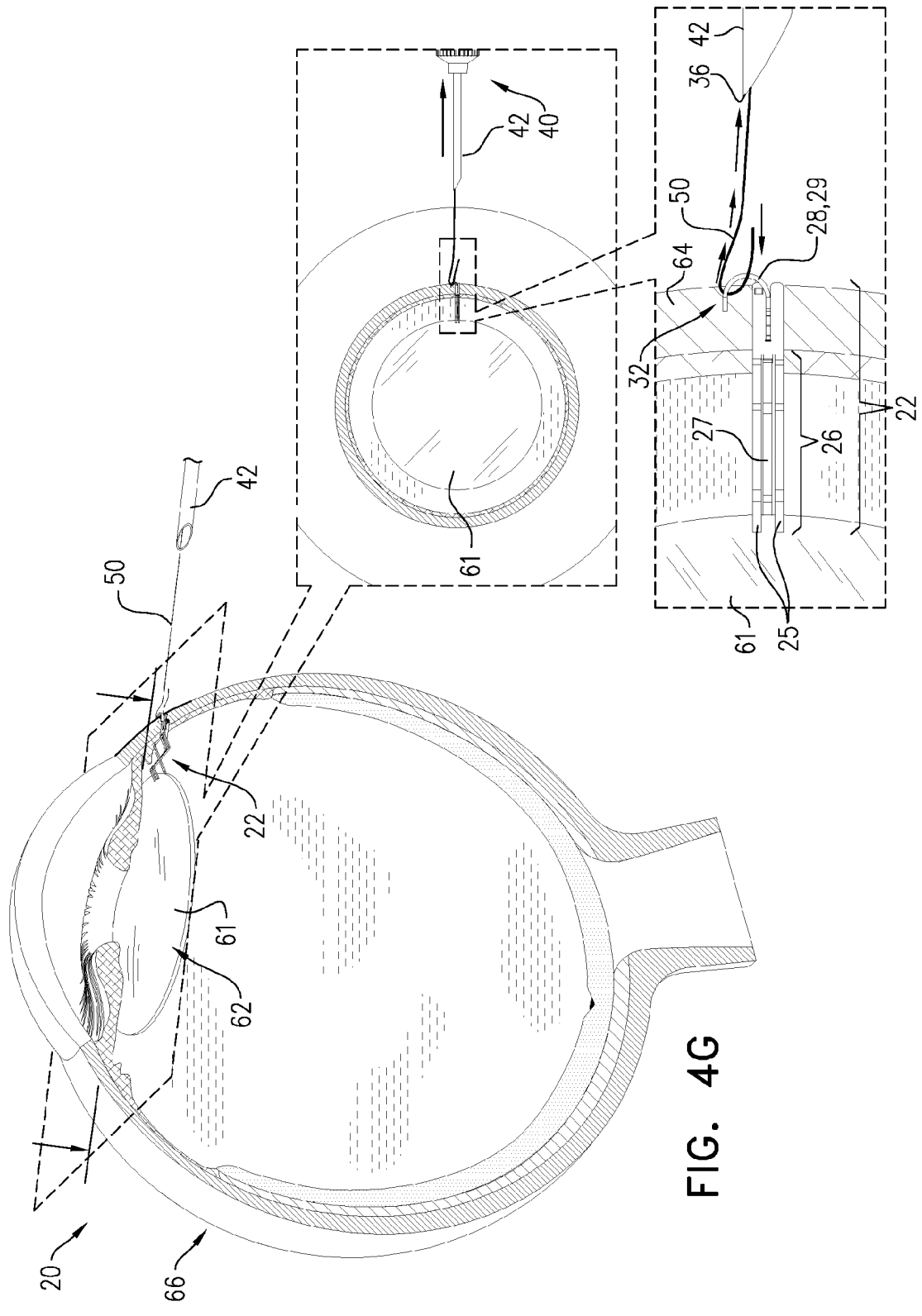
Figure 4H:
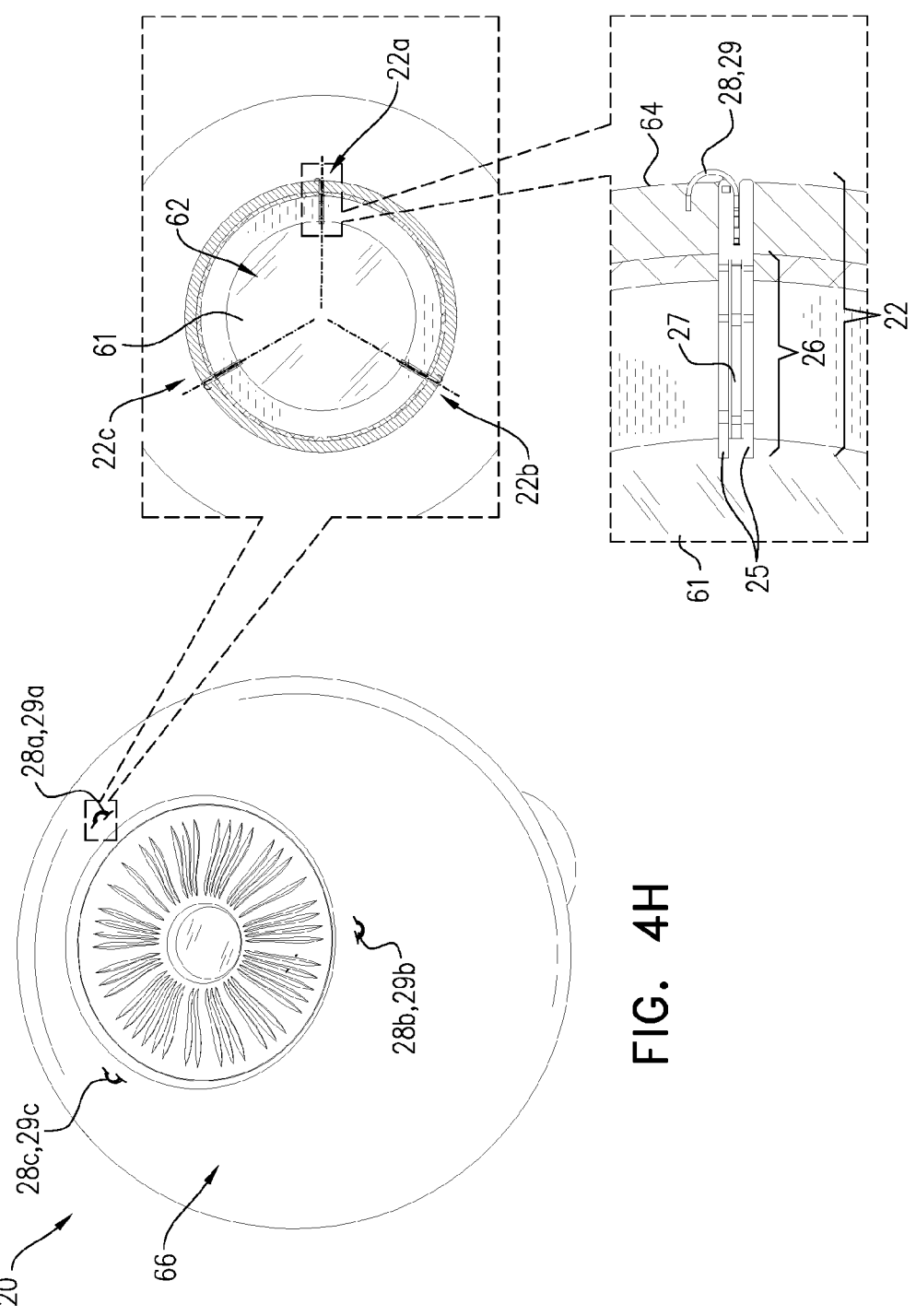

Once anchor 29 is deployed, introduction sheath 42 is retracted, as shown in FIG. 4H. Retracting of sheath 42 helps to disengage instrument 40 from implant 22. Disengagement of instrument 40 may happen at this step or after the next step shown in FIG. 4G. Disengagement of instrument 40 occurs by decoupling hook 41, e.g., by moving or tilting of shaft 44, from opening 34 of implant 22, and by decoupling hook 43. e.g., by moving or tilting shaft 46, from opening 30 of implant 22.

As noted hereinabove, during grasping and repositioning of IOL 62 as well as retracting of instrument 40 through wall 64 at entry point 60, suture 50 remains coupled to ocular-wall-engaging portion 28, e.g., by being looped through opening 32 in anchor 29 and by running through a portion of the sclera to outside eye 66. Suture 50 remains coupled to ocular-wall-engaging portion 28 even after deployment of anchor 29. As long as suture 50 remains coupled to ocular-wall-engaging portion 28, the operating physician can deform anchor 29 to a different configuration, e.g., a straightened configuration, by pulling on suture 50 in order to apply pressure to anchor 29, as is described hereinbelow with reference to FIGS. 5A-C.

As shown in FIG. 4G, once the physician is satisfied with both the repositioning of IOL 62 and the positioning of anchor 29, the physician releases one end of suture 50 and pulls on the second end of suture 50 so that suture 50 slides with respect to opening 32 of anchor 29 until suture 50 is decoupled from ocular-wall-engaging portion 28.

Instrument 40 may then be decoupled from implant 22, as described hereinabove, and instrument 40 is retracted out of the eye. For some applications, even after instrument 40 is decoupled from implant 22, suture 50 remains coupled to ocular-wall-engaging portion 28. Suture 50 is then decoupled from ocular-wall-engaging portion 28 at a later stage.

For some applications, once ocular-wall-engaging portion 28 has been anchored to wall 64, suture 50 remains coupled to ocular-wall-engaging portion 28 and passes out of entry point 60. In such applications, suture 50 bolsters anchoring of implant 22 by the operating physician using thermal cautery or any other device to melt suture 50 into a flat structure, e.g., a disc, at the sclera such that the flat structure rests against the outer surface of the scleral wall.

FIG. 4H shows a plurality of implants 22. e.g., three implants 22a, 22b, and 22c, being coupled to the eye at different locations in a manner as described hereinabove with reference to FIGS. 3 and 4A-G. The number of implants 22 is determined by the operating physician in order to successfully reposition and fixate intraocular IOL 62.

Figure 5A:
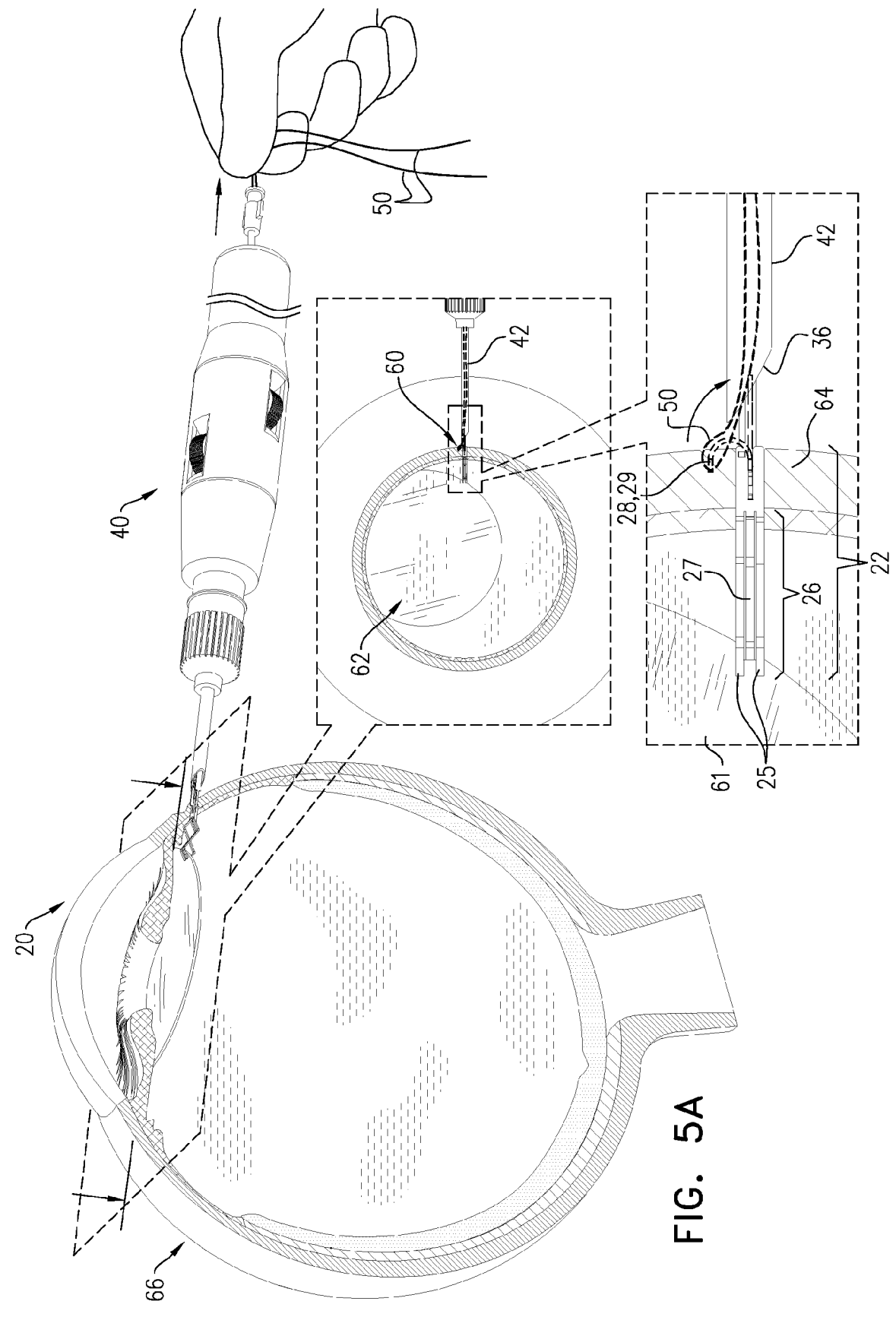
FIGS. 5A-C are schematic illustrations of an example of a method for repositioning the ocular clip implant following initial implantation using the introduction instrument of FIGS. 1A-B and 2, in accordance with some applications of the present invention.
Figure 5B:
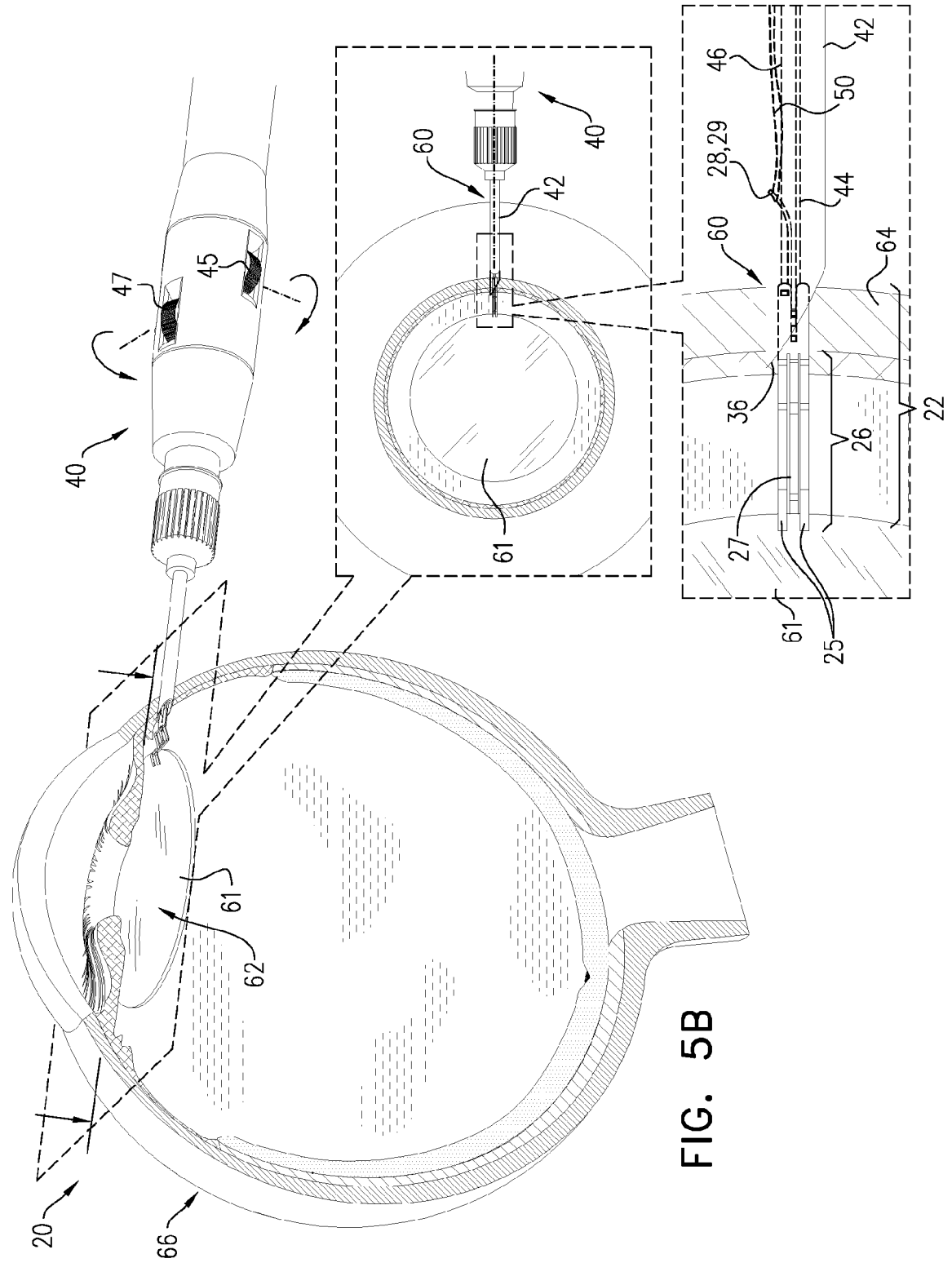
Figure 5C:
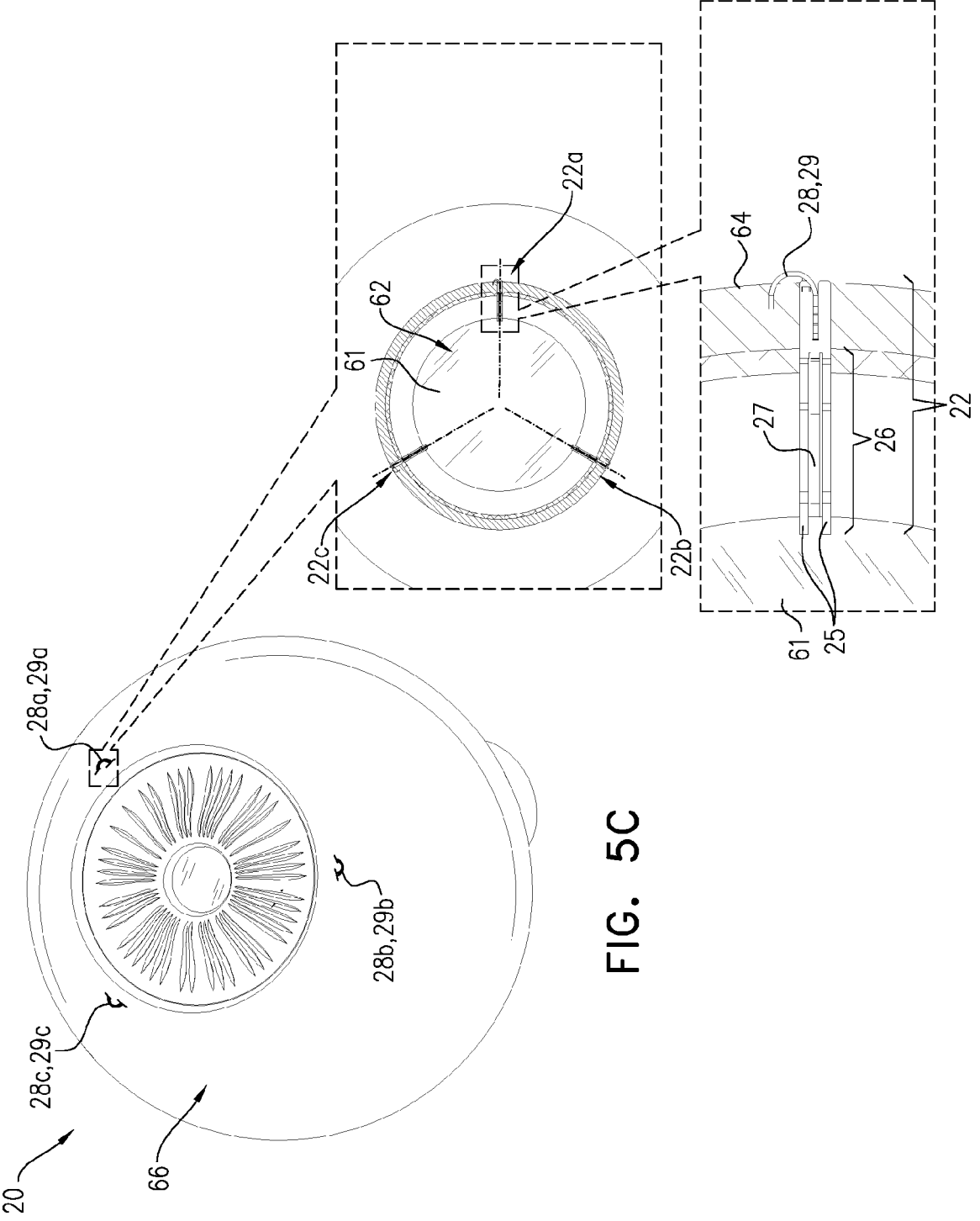
Figure 6:
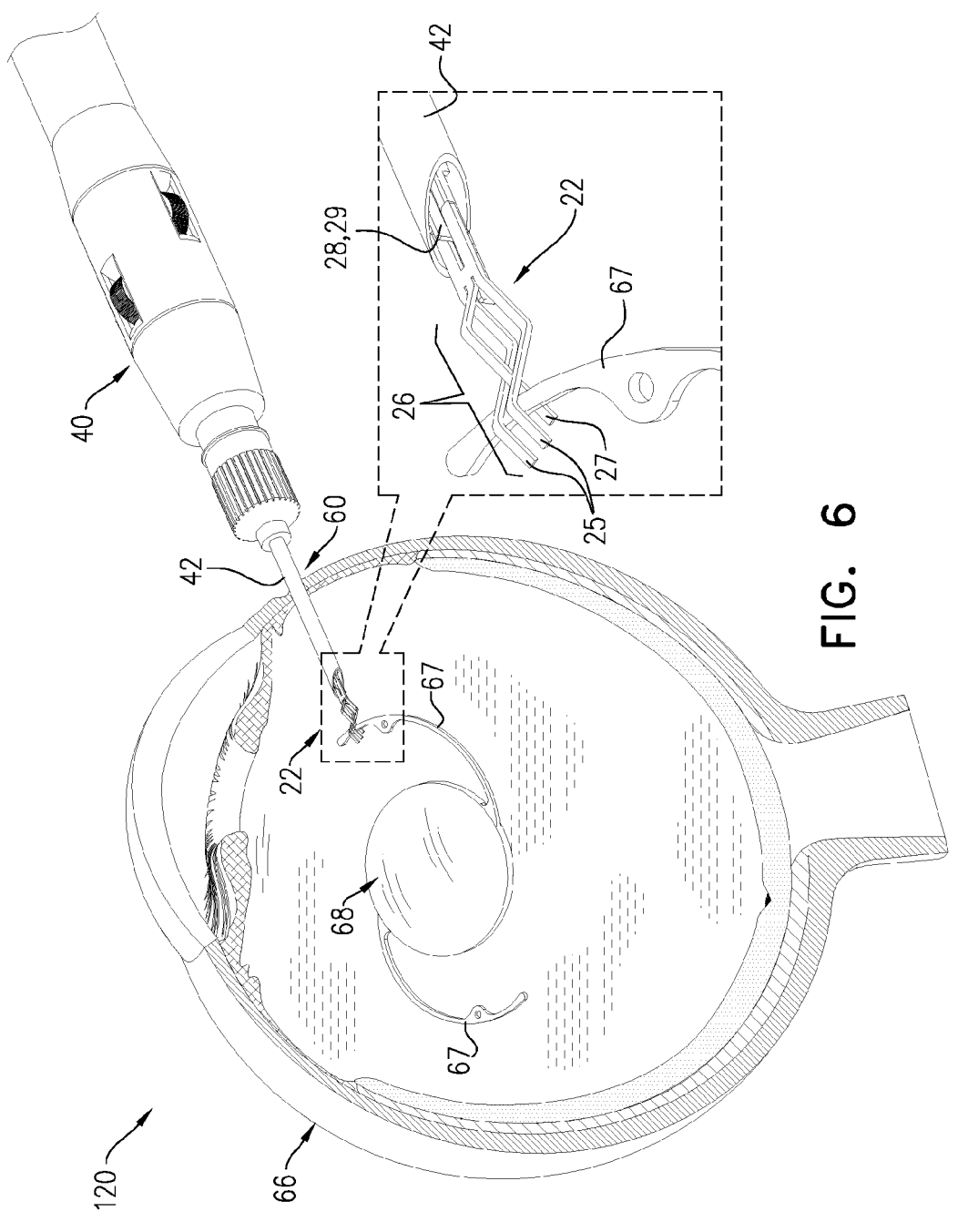
FIG. 6 is a schematic illustration of an example of a method for using the introduction instrument of FIGS. 1A-B and 2 in order to implant the ocular clip implant for fixation of an intraocular lens (IOL), in accordance with some other applications of the present invention.

Reference is now made to FIGS. 5A-C, which are schematic illustrations of an example of a method for repositioning ocular clip implant 22 following initial implantation using introduction instrument 40, in accordance with some applications of the present invention. FIGS. 5A-C show how the initial anchoring of implant 22 by anchor 29 is reversible. If the physician finds that either IOL 62 or anchor 29 is not appropriately positioned, system 20 provides a mechanism by which anchoring of ocular-wall-engaging portion 28 is reversible so that the physician can either reposition anchor 29 and, if necessary, also further reposition IOL 62 before deploying anchor 29 again.

As shown in FIG. 5A, anchor 29 is in its second, non-straightened configuration, e.g., curved, as shown, after it has been deployed in wall 64 of eye 66. Instrument 40 is still coupled to implant 22 either because suture 50 is still coupled to ocular-wall-engaging portion 28 and/or because hook 41 of shaft 44 is still engaged with opening 34 of implant 22 and hook 43 of shaft 46 is still engaged with opening 30 of implant 22. Anchor 29 of ocular-wall-engaging portion 28 may be transitioned back to its first, generally straightened, or straightened, configuration by deforming anchor 29 from its second, non-straightened configuration back to its generally-straightened, or straightened, configuration upon application of a force to ocular-wall-engaging portion 28. The application of the force to ocular-wall-engaging portion 28 is accomplished by pulling on suture 50 from a site outside the eye, e.g., either by the operating physician pulling on suture 50, as shown, or by pulling on instrument 40.

Once anchor 29 is straightened, as shown in FIG. 5B, it can be retracted back into sheath 42 so that sheath 42 may reenter the eye through the same entry point 60 in order to cither reposition anchor 29 and/or further reposition IOL 62. If the operating physician wishes to further reposition IOL 62, since IOL-engaging portion 26 remains coupled to IOL 62, the operating physician moves instrument 40 in order to further reposition IOL 62. Once satisfied with the position of IOL 62, instrument 40 is retracted, as described hereinabove with reference to FIG. 4D, in order to retract sheath 42 through entry point 60. Anchor 29 is then re-anchored to wall 64 of eye as described hereinabove with reference to FIGS. 4E-G.

FIG. 5C shows a plurality of implants 22, e.g., three implants 22a, 22b, and 22c, being coupled to the eye at different locations in a manner as described hereinabove with reference to FIGS. 3 and 4A-G. The number of implants 22 is determined by the operating physician in order to successfully reposition and fixate IOL 62.

Reference is now made to FIG. 6, which is a schematic illustration of a system 120 for repositioning and securing a dislocated IOL 68 comprising haptics 67 using implant 22 using introduction instrument 40, in accordance with some applications of the present invention. Jaws 25 and 27 engage haptic 67, as shown. For some applications, jaws 25 and 27 are curved, or IOL-engaging portion 26 is shaped so as to provide engagers or graspers which are curved (configuration not shown), so as to cup haptic 67.

Methods for securing and repositioning IOL 68 by grasping haptic(s) 67 using system 120 are similar to those described hereinabove with regard to system 20 with reference to FIGS. 3-4H, mutatis mutandis. Additionally, methods for reversible anchoring of ocular-wall-engaging portion 28 of system 120 are similar to those described hereinabove with regard to system 20 with reference to FIGS. 5A-C, mutatis mutandis.

Reference is now made to FIGS. 1A-6. It is to be noted that implant 22 grasps a haptic of IOL 62 or may be shaped and configured for grasping a haptic of IOL 62, mutatis mutandis. It is also to be noted that systems 20 and 120 described herein may be used for grasping and securing IOL 62, IOL 68 or any other IOL known in the art, and optionally, system 20 may be used for repositioning IOL 62, IOL 68 or any other IOL known in the art. It is to be noted that implant 22 grasps or may be shaped and configured for grasping any portion of the IOL, mutatis mutandis. For some applications, systems 20 and 120 described herein may be used for grasping, securing, and optionally repositioning, capsular tension rings (CTRs), modified capsular tension rings (e.g., Cionni capsular tension rings), Ahmed segments, Assia Anchors, capsular tension segments, capsular retention hooks, and/or any other capsular support devices known in the art.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An ocular clip implant used for securing an intraocular lens (IOL) in an eye of a patient, the ocular clip implant comprising:

an IOL-engaging portion disposed at a first end of the ocular clip implant, the IOL-engaging portion:

being configured to grasp a portion of the IOL, and comprising first and second opposing jaws which are moveable with respect to each other to grasp the portion of the IOL, the first jaw being positionable against a first surface of the portion of the IOL at a first location to apply pressure to the first surface of the portion of the IOL, and the second jaw being positionable against a second surface of the portion of the IOL at the first location to apply pressure to the second surface of the portion of the IOL; and an ocular-wall-engaging portion integrated with and disposed at a second end of the ocular clip implant, the ocular-wall-engaging portion comprising an anchor transitionable from a first, straightened configuration to a second, non-straightened configuration to anchor the ocular clip implant to a wall of the eye in order to secure the IOL to the eye.

2. The ocular clip implant according to claim 1, wherein the anchor has a pointed tip configured to pierce the wall of the eye in order to secure the IOL to the eye.

3. The ocular clip implant according to claim 1, wherein the anchor of the ocular-wall-engaging portion comprises at least one hook transitionable from the straightened configuration to a curved configuration to anchor the ocular clip implant to the wall of the eye.

4. The ocular clip implant according to claim 1, wherein the first and second opposing jaws comprise shape-memory material, and wherein the jaws are configured to assume a closed state in an absence of force applied thereto.

5. A system comprising the ocular clip implant according to claim 1, the system further comprising an introduction instrument comprising an introduction sheath configured to house and deliver the ocular clip implant, wherein the anchor of the ocular clip implant is disposed within the introduction sheath in the first, straightened configuration, and wherein the anchor of the ocular clip implant is deformable to the second, non-straightened configuration when exposed from within the introduction sheath.

6. The system according to claim 5, wherein the introduction instrument is configured to deliver the ocular clip implant through an entry point in the eye, facilitate grasping of the portion of the IOL by the IOL-engaging portion through the entry point, and facilitate anchoring of the ocular clip implant by the anchor of the ocular-wall-engaging portion through the entry point.

7. A system comprising the ocular clip implant according to claim 1, the system further comprising an introduction instrument comprising an introduction sheath configured to house and deliver the ocular clip implant, wherein the ocular clip implant is disposed within the introduction sheath with the anchor of the ocular-wall-engaging portion in the first, straightened configuration, and wherein the anchor of the ocular-wall-engaging portion comprises a shape-memory material that is configured to deflect the anchor away from an axis of a lumen of the introduction sheath when the anchor is exposed from within the introduction sheath.

8. An ocular clip implant used for securing an intraocular lens (IOL) in an eye of a patient, the ocular clip implant comprising:

an IOL-engaging portion disposed at a first end of the ocular clip implant, the IOL-engaging portion being configured to grasp a portion of the IOL; and an ocular-wall-engaging portion integrated with and disposed at a second end of the ocular clip implant, the ocular-wall-engaging portion comprising an anchor, the anchor:

being reversibly transitionable from a first, straightened configuration to a second, non-straightened configuration to anchor the ocular clip implant to a wall of the eye in order to secure the IOL to the eye, comprising a shape-memory material which transitions the anchor of the ocular-wall-engaging portion from the first, straightened configuration to the second, non-straightened configuration, and being deformable from the second, non-straightened configuration upon application of a force to the ocular-wall-engaging portion, wherein the ocular-wall-engaging portion is shaped so as to define an opening for reversible coupling of a suture to the ocular-wall-engaging portion, and wherein application of a pulling force to the suture facilitates application of the force to the ocular-wall-engaging portion to deform the anchor of the ocular-wall-engaging portion from the second configuration.

9. The ocular clip implant according to claim 8, wherein the IOL-engaging portion is configured to grasp an optic of the IOL, and wherein the first and second opposing jaws have textured, ridged, or serrated surfaces which increase friction between the IOL-engaging portion and the optic of the IOL.

10. A method for securing an intraocular lens (IOL) in an eye of a patient, the method comprising:

introducing within the eye through an entry point in the eye an IOL-engaging portion of an ocular clip implant, the IOL-engaging portion disposed at a first end of the ocular clip implant;

grasping a portion of the IOL with the IOL-engaging portion by moving first and second opposing jaws of the IOL-engaging portion with respect to each other, and by the moving:

positioning the first jaw against a first surface of the portion of the IOL at a first location;

positioning the second jaw against a second surface of the portion of the IOL at the first location; and applying pressure to the first and the second surfaces of the portion of the IOL by the first and the second jaws, respectively;

securing the IOL to the eye by anchoring the ocular clip implant to a wall of the eye by:

positioning an ocular-wall-engaging portion integrated with and disposed at a second end of the ocular clip implant, partially within the wall of the eye and through the entry point and partially proximally to the wall of the eye; and facilitating transitioning of an anchor of the ocular-wall-engaging portion from a first, straightened configuration to a second, non-straightened configuration.

11. The method according to claim 10, wherein anchoring the ocular clip implant to the wall of the eye comprises piercing the wall of the eye with the anchor of the ocular-wall-engaging portion.

12. The method according to claim 10, wherein the method further comprises, subsequently to the grasping, repositioning the IOL within the eye by moving the IOL with the IOL-engaging portion grasped thereto.

13. The method according to claim 12, wherein anchoring the ocular clip implant comprises reversibly anchoring the ocular clip implant by applying a force to the ocular-wall-engaging portion, and wherein applying the force to the ocular-wall-engaging portion comprises deforming the anchor of the ocular-wall-engaging portion from the second, non-straightened configuration to the first, straightened configuration.

14. The method according to claim 13, wherein the method further comprises:

further repositioning the IOL coupled to IOL-engaging portion via the entry point subsequently to the deforming the anchor of the ocular-wall-engaging portion; and subsequently, re-anchoring the ocular clip implant to the wall of the eye by:

repositioning the anchor of the ocular-wall-engaging portion partially within the wall of the eye and through the entry point and partially proximally to the wall of the eye; and facilitating transitioning of the anchor of the ocular-wall-engaging portion from the first, straightened configuration to the second, non-straightened configuration.

15. The method according to claim 10, wherein anchoring the ocular clip implant to the wall of the eye comprises:

delivering the ocular clip implant to the eye while the anchor of the ocular-wall-engaging portion is disposed in the straightened configuration within a lumen of an introduction sheath; and facilitating the transitioning of the anchor of the ocular-wall-engaging portion from the first, straightened configuration to the second, non-straightened configuration by exposing the anchor of the ocular-wall engaging portion such that a shape-memory material of the anchor deflects the anchor away from an axis of the lumen of the introduction sheath.

\* \* \* \* \*